US009880159B2

(12) United States Patent
Powers et al.

(10) Patent No.: US 9,880,159 B2
(45) Date of Patent: Jan. 30, 2018

(54) CARTRIDGE-BASED DETECTION SYSTEM

(71) Applicants: Linda S. Powers, Tucson, AZ (US);
Kevin M. Okarski, Tucson, AZ (US);
Walther R. Ellis, Jr., Tucson, AZ (US)

(72) Inventors: Linda S. Powers, Tucson, AZ (US);
Kevin M. Okarski, Tucson, AZ (US);
Walther R. Ellis, Jr., Tucson, AZ (US)

(*) Notice: Subject to any disclaimer, the term of this patent is extended or adjusted under 35 U.S.C. 154(b) by 0 days.

(21) Appl. No.: 14/872,840

(22) Filed: Oct. 1, 2015

(65) Prior Publication Data

US 2016/0097763 A1 Apr. 7, 2016

Related U.S. Application Data

(60) Provisional application No. 62/058,216, filed on Oct. 1, 2014.

(51) Int. Cl.
*G01N 33/53* (2006.01)
*B01L 3/00* (2006.01)

(52) U.S. Cl.
CPC .... *G01N 33/5302* (2013.01); *B01L 3/502715* (2013.01); *B01L 3/502738* (2013.01); *B01L 3/527* (2013.01); *B01L 2200/027* (2013.01); *B01L 2200/0621* (2013.01); *B01L 2300/044* (2013.01); *B01L 2300/0672* (2013.01); *B01L 2300/0809* (2013.01); *B01L 2300/0864* (2013.01); *B01L 2300/0887* (2013.01); *B01L 2400/0622* (2013.01); *B01L 2400/0683* (2013.01)

(58) Field of Classification Search
None
See application file for complete search history.

(56) References Cited

U.S. PATENT DOCUMENTS

| 6,750,006 B2 | 6/2004 | Powers et al. |
| 6,780,602 B2 | 8/2004 | Powers et al. |
| 7,186,990 B2 | 3/2007 | Powers et al. |

(Continued)

FOREIGN PATENT DOCUMENTS

| CN | 101495869 | | 7/2009 | |
| WO | WO 2014143010 | * | 9/2014 | ........ B01L 3/502715 |

OTHER PUBLICATIONS

Rice University. "Rice University Makes First Rapid, Sensitive Whole-blood Immunoassay: Innovative Test Based on Nanoshells Could Provide Critical Info for ER Doctors, Others." ScienceDaily. ScienceDaily, Aug. 4, 2003. <www.sciencedaily.com/releases/2003/07/030725075225.htm>.

*Primary Examiner* — P. Kathryn Wright
(74) *Attorney, Agent, or Firm* — Klarquist Sparkman, LLP

(57) ABSTRACT

Disclosed is a cartridge-based detection system to prepare an injected sample to be investigated for determination of a microbial pathogen or another analyte of interest using a detector features a field-safe cartridge. The system features a plurality of reagent chambers located within the cartridge. The system features a rotating cylindrical dial that facilitates a sequential introduction of various fluids contained in each reagent chamber into the dial whereby the fluid washes internally for contact therein. A dial channel is located through the dial. A dual window region of interrogation is centrally located in the dial. The dial is pivoted into position to fluidly connect each mated anterior and posterior reagent chamber via the dial channel. Methods of used are also disclosed.

20 Claims, 18 Drawing Sheets

(56) References Cited

U.S. PATENT DOCUMENTS

| | | |
|---|---|---|
| 7,211,377 B1 | 5/2007 | Powers et al. |
| 7,595,196 B2 | 9/2009 | Guo et al. |
| 7,824,883 B2 | 11/2010 | Powers et al. |
| 7,897,360 B2 | 3/2011 | Song |
| 7,932,099 B2 | 4/2011 | Egan et al. |
| 8,216,797 B2 | 7/2012 | Schwoebel et al. |
| 8,697,007 B2 * | 4/2014 | Bau et al. |
| 2010/0252116 A1 * | 10/2010 | Kilcoin ................ B01L 3/0293 137/1 |
| 2012/0111719 A1 | 5/2012 | Kendig et al. |

* cited by examiner

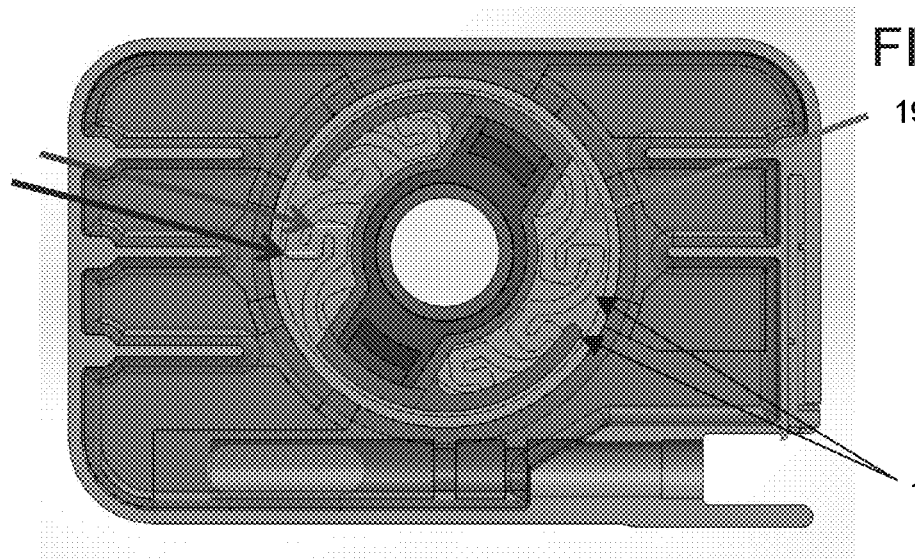

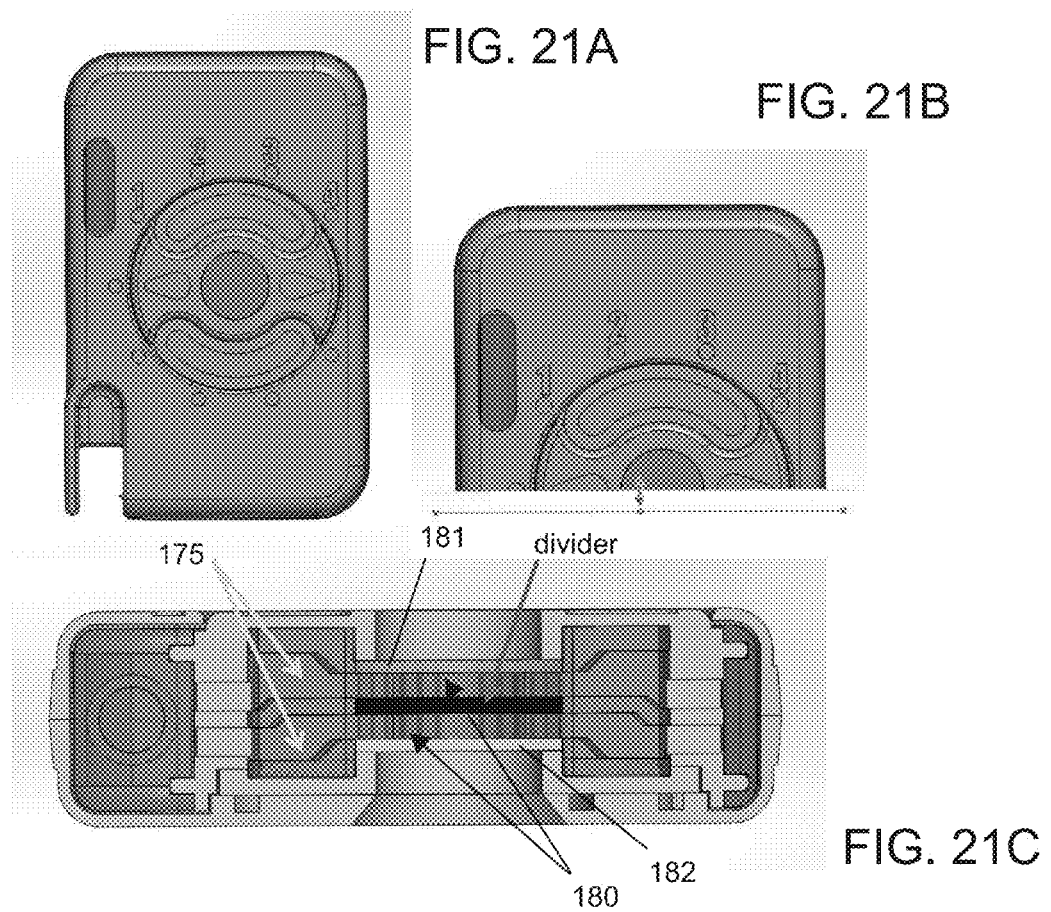

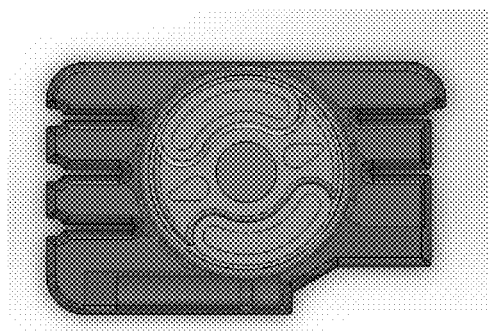
FIG. 22A
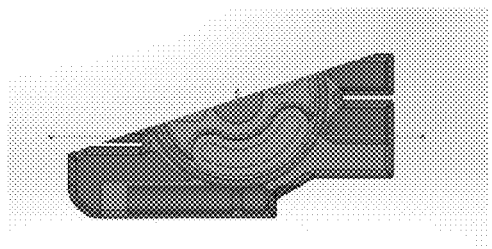
FIG. 22B
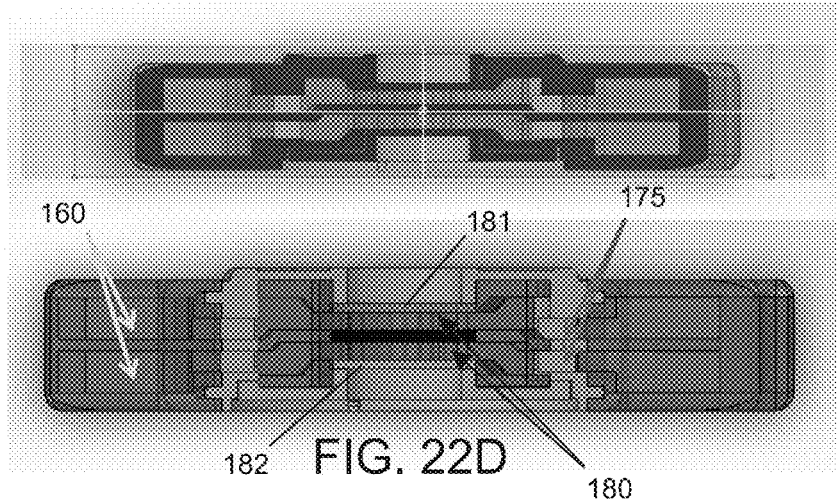
FIG. 22C
FIG. 22D

CARTRIDGE-BASED DETECTION SYSTEM

CROSS REFERENCE TO RELATED APPLICATION

This application claims the benefit of U.S. Provisional Patent Application No. 62/058,216, filed on Oct. 1, 2014, which is incorporated herein by reference in its entirety.

ACKNOWLEDGEMENT OF GOVERNMENT SUPPORT

This invention was made with government support under Grant Nos. M67854-12-C-6530 awarded by Department of Defense Marine Corps Systems Command and Grant No. N00014-12-C-0540 awarded by the Office of Naval Research. The government has certain rights in the invention.

FIELD

This disclosure relates to assay systems, and in particular to cartridge-based detection systems and methods of use thereof, including identification of microbial pathogens or other analytes.

BACKGROUND

Field conditions such as those found on a battlefield or in some types of remote environments most often do not support the use or presence of laboratory facilities or the type of equipment used therein, making it difficult to test for and identify the presence of microbial pathogens or other analytes of interest in a sample to be investigated such as blood. A durable, yet disposable, self-contained assay system is needed for identification of the presence of microbial pathogens or other analytes of interest in field conditions.

SUMMARY

The present disclosure pertains to assay systems for use in field conditions. In particular, disclosed herein is a disposable cartridge-based detection system to prepare an injected sample to be investigated for determination of microbial pathogens or other analytes of interest using a detector. Other than the sample to be investigated, no other reagents are injected into the cartridge. The cartridge is designed to contain all medical waste, including the syringe used to inject the patient sample, thus facilitating quick and safe disposal.

In some embodiments, the system comprises a field-safe cartridge. In some embodiments, a syringe port is located on a cartridge posterior end close to a cartridge first side. In some embodiments, a cylindrical syringe channel is located in the cartridge between a septum and the syringe port and fluidly connected to the syringe port. In some embodiments, an elastomeric first collar is located in the syringe channel next to the syringe port. In some embodiments, an elastomeric second collar is located in the syringe channel close to the first collar. In some embodiments, the first collar and the second collar each comprise a diameter smaller than a diameter of the syringe channel for sealing against a body of a syringe upon insertion of the syringe. In some embodiments, a syringe channel volume is greater than a volume of the syringe. In some embodiments, a tapered syringe lock is located on a sidewall of the syringe channel.

In some embodiments, a locking tab is located in a locking tab channel. In some embodiments, the locking tab channel having a locking tab channel anterior side and a locking tab channel posterior side is located on the cartridge posterior end. In some embodiments, a first locking tab stop is located on the locking tab channel posterior side next to the syringe port. In some embodiments, a second locking tab stop is located on the locking tab channel posterior side at a distance equal to a locking tab length from an opposite sidewall of the syringe channel. In some embodiments, a tensioning projection is located on the locking tab channel anterior side between the first locking tab stop and the second locking tab stop.

In some embodiments, the system comprises a plurality of reagent chambers located in the cartridge comprising an anterior first reagent chamber, a posterior first reagent chamber, a plurality of sequentially mated anterior and opposing posterior reagent chambers, and a final anterior reagent chamber. In some embodiments, a first anterior reagent chamber is next to the septum.

In some embodiments, the system comprises a rotating cylindrical dial. In some embodiments, the dial facilitates a sequential introduction of various fluids contained in each reagent chamber into the dial whereby the fluid washes internally for contact therein. In some embodiments, the dial is centrally located in the cartridge from a cartridge top surface. In some embodiments, the dial extends through the cartridge to engage an inside wall of the cartridge bottom surface. In some embodiments, the dial comprises a dial thickness from the dial top surface to the dial bottom surface about equal to the cartridge thickness. In some embodiments, a dial channel is located through the dial from a first position on the dial side wall to a second position on an opposing side of the dial side wall. In some embodiments, a dual window region of interrogation is centrally located in the dial. In some embodiments, the dial channel is located between a top window and a bottom window. In some embodiments, a cross section of the dial channel is greater at the first position on the dial side wall and the second position on the dial side wall than the dial channel between the top window and the bottom window of the region of interrogation. In some embodiments, a cross-sectional area of the dial channel reduces towards the region of interrogation and increases towards the dial side wall. In some embodiments, the number of analytes to be captured can be doubled by employing a double-stacked cartridge, the portion of each side interrogated by the detector being separated by an impenetrable wall. For example FIGS. 21A-23 show a bifurcated dial channel, the top window, and the bottom window. In some embodiments, a divider in the dial channel has dual functionality as a light stop and as a functionalized surface for capturing analytes of interest. In some embodiments, both sides would be functionalized so as to capture targets flowing through the bifurcated channels. In some embodiments, the divider is not limited to serving both functions, it may solely act as either a divider or as a light stop. In some embodiments, the divider would be sandwiched between two additional quartz (or other material transparent to the method of measurement) discs that are functionalized for target capture. In some embodiments, the inlay is not limited to the depicted configurations. In some embodiments, the inlay could potentially consists of a single set of paired reservoirs or a bifurcated/double-stacked version of such a configuration depending on the sample being processed or detection method being used.

In some embodiments, the dial is rotated into position to fluidly connect each mated anterior and posterior reagent chamber via the dial channel. In some embodiments, the dial comprises a first dial indentation and a second dial indentation adapted to receive a finger or a thumb inserted therein for rotating the dial. In some embodiments, the dial comprises a ratchet mechanism to facilitate a correct, sequential exposure of the injected patient sample to reagents contained within the cartridge. In some embodiments, upon rotation of the dial in a clockwise manner to a first position, the dial hits a first front stop. In some embodiments, upon rotation of the dial in a counterclockwise manner, the dial hits a first back stop. In some embodiments, upon rotation of the dial in a clockwise manner to a next position, the dial hits a next front stop. In some embodiments, upon rotation of the dial in a counter clockwise manner, the dial hits a next back stop. In some embodiments, upon rotation of the dial in a clockwise manner to a last position, the dial hits a last front stop. In some embodiments, upon rotation of the dial in a counter clockwise manner, the dial hits a last back stop.

In some embodiments, the system comprises a syringe having a needle.

In some embodiments, a user draws fluid into the syringe. In some embodiments, the user inserts the syringe into the syringe channel. In some embodiments, the syringe body slides through the first collar and the second collar. In some embodiments, the first collar and the second collar snuggly hold the syringe into the syringe channel. In some embodiments, the syringe needle pierces the septum. In some embodiments, a syringe back edge slides past the syringe lock until the syringe lock snaps over the syringe back edge locking it into position. In some embodiments, the user activates the syringe dispensing the fluid into the first anterior reagent chamber where it mixes with another fluid. In some embodiments, the locking tab is depressed toward the body of the cartridge to release it from the first locking tab stop and moved to the second position to cover the syringe channel and block the syringe from removal. In some embodiments, the second locking tab stop prevents the locking tab from sliding back to the first position. In some embodiments, the dial is positioned to a first position to expose the injected sample to cytolytic conditions, causing patient cells to lyse and release any microorganisms inside the cells. In some embodiments, the cells are red blood cells or another type of cell. In some embodiments, the device is agitated to flush the fluid across the region of interrogation between the first anterior reagent chamber and the first posterior reagent chamber. In some embodiments, modified Taylor flow or Slug flow from formed bubbles causes the microbial pathogens and other analytes of interest to be driven close to the inside surface of the region of interrogation to be captured onto a chemically coated surface. In some embodiments, the dial is positioned into a next position to expose the captured analytes to a molecular tag, such as a fluorescent dye conjugated to a molecule that binds to the analyte, that can be sensed by the detector. In some embodiments, the device is agitated to flush the fluid across the region of interrogation between the next anterior reagent chamber and the next posterior reagent chamber. In some embodiments, the dial is positioned into a next position, then agitated, to remove excess tag molecules. In some embodiments, the dial is position into a last position to introduce and seal fluid into a final anterior reagent chamber.

Any feature or combination of features described herein are included within the scope of the present disclosure provided that the features included in any such combination are not mutually inconsistent as will be apparent from the context, this specification, and the knowledge of one of ordinary skill in the art. Additional advantages and aspects of the present disclosure are apparent in the following detailed description, which proceeds with reference to the accompanying figures.

BRIEF DESCRIPTION OF THE DRAWINGS

FIG. 19 shows a top view of the inside of the cartridge and bottom side of the dial featuring the ratchet mechanism. The ratchet grooves which guide the ratchet arms through the stage selection process are highlighted. The top, left arrow points to the first stage of the ratcheting process. The wall prevents the user from continually turning the dial clockwise and potentially overshooting or skipping paired reagent chamber stages. The overlapping ledges form radial paths that release compression of the ratchet arms generating audible and tactile feedback for the user. The bottom left arrow points to the second stage of the ratcheting process that is reached through counter-clockwise turning of the dial. The wall prevents further counter-clockwise turning of the dial. The dial may now be turned clockwise again to proceed to the next stage. The right arrow points to the ramp portion of the ratchet groove that provides increasing resistance that has two functions—compression of the ratchet arms and tactile feedback for the user. The greater the resistance, the closer the user is getting to the first state of the ratchet process.

FIG. 21A shows a top view of an alternate view of the cartridge of the present disclosure.

FIG. 21B shows a close up view of an alternate embodiment of the cartridge of the present disclosure.

FIG. 21C shows a cross-section of an alternate embodiment of the region of interrogation of the present disclosure featuring a bifurcated dial channel, the top window, and the bottom window in a double-stacked configuration. A divider in the dial channel has dual functionality as a light stop and as a functionalized surface for capturing targets of interest. Both sides would be functionalized so as to capture targets flowing through the bifurcated channels. The divider is not limited to serving both functions, it may solely act as either a divider or as a light stop. In such an instance, the divider would be sandwiched between two additional quartz (or other material transparent to the method of measurement) discs that are functionalized for target capture.

FIG. 22A shows a top view of the cartridge with the dial in place in a second position.

FIG. 22B shows a cross-section taken through Stage 2.

FIG. 22C shows a cross-section of an alternate embodiment of the region of interrogation of the present disclosure at Stage 2 in a double-stacked configuration.

FIG. 22D shows a cross-section of an alternate embodiment of the region of interrogation of the present disclosure at Stage 2 featuring a double-stacked or bifurcated outer inlay interface with bifurcated dial and central inlay.

DETAILED DESCRIPTION OF SEVERAL EMBODIMENTS

Figure 1:
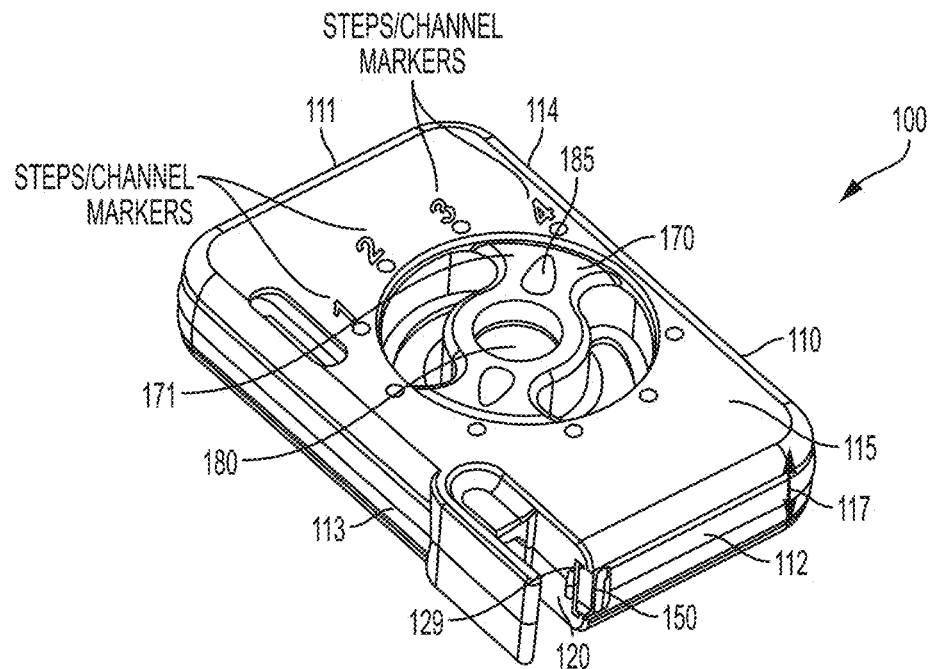
FIG. 1 shows a perspective view of a disclosed embodiment, cartridge based detection system 100.
Figure 2:
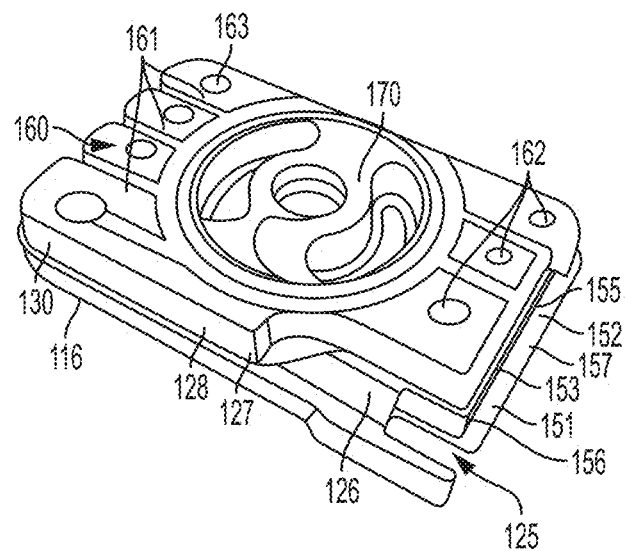
FIG. 2 shows a perspective view of system 100 with a top cover removed.
Figure 3:
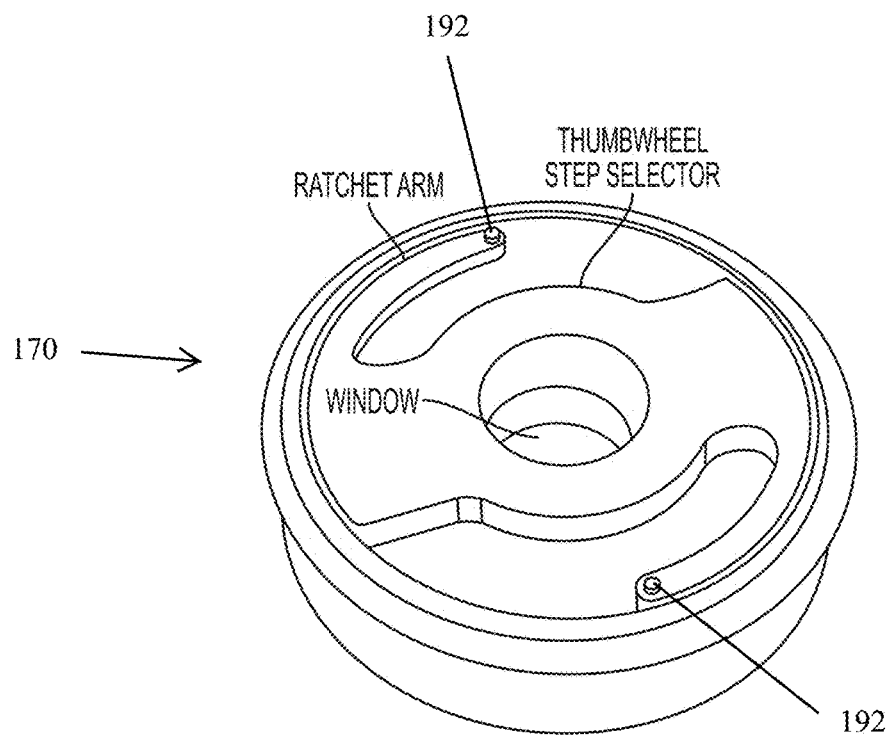
FIG. 3 shows a perspective view of dial 170 of system 100.
Figure 4:
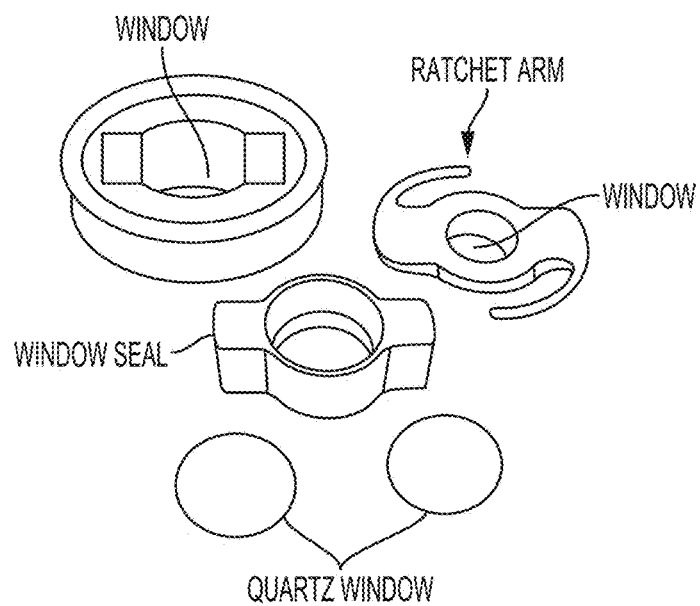
FIG. 4 shows a perspective view of multiple components of dial 170.
Figure 5:
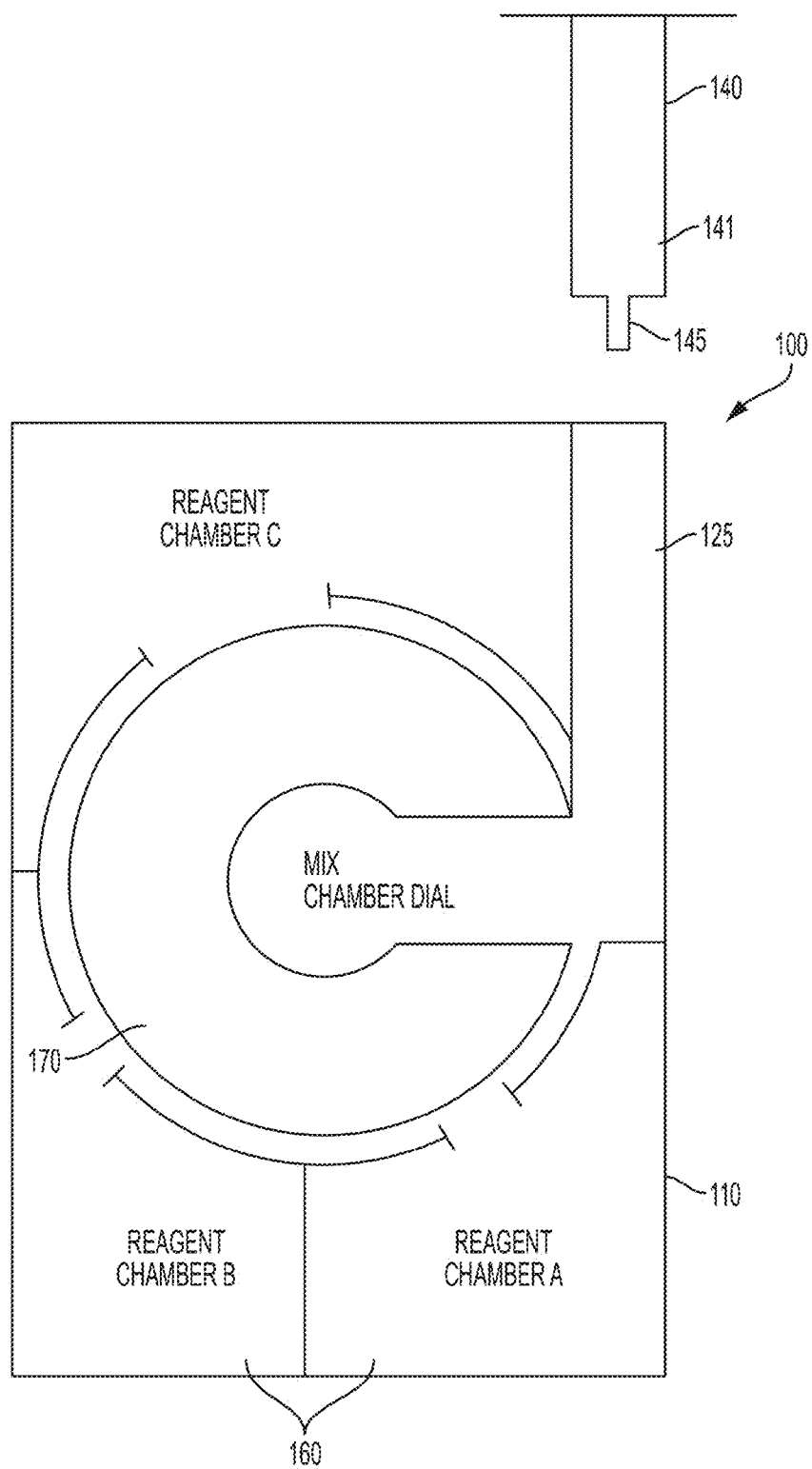
FIG. 5 shows a top view of an alternate embodiment of the present disclosure.
Figure 6:
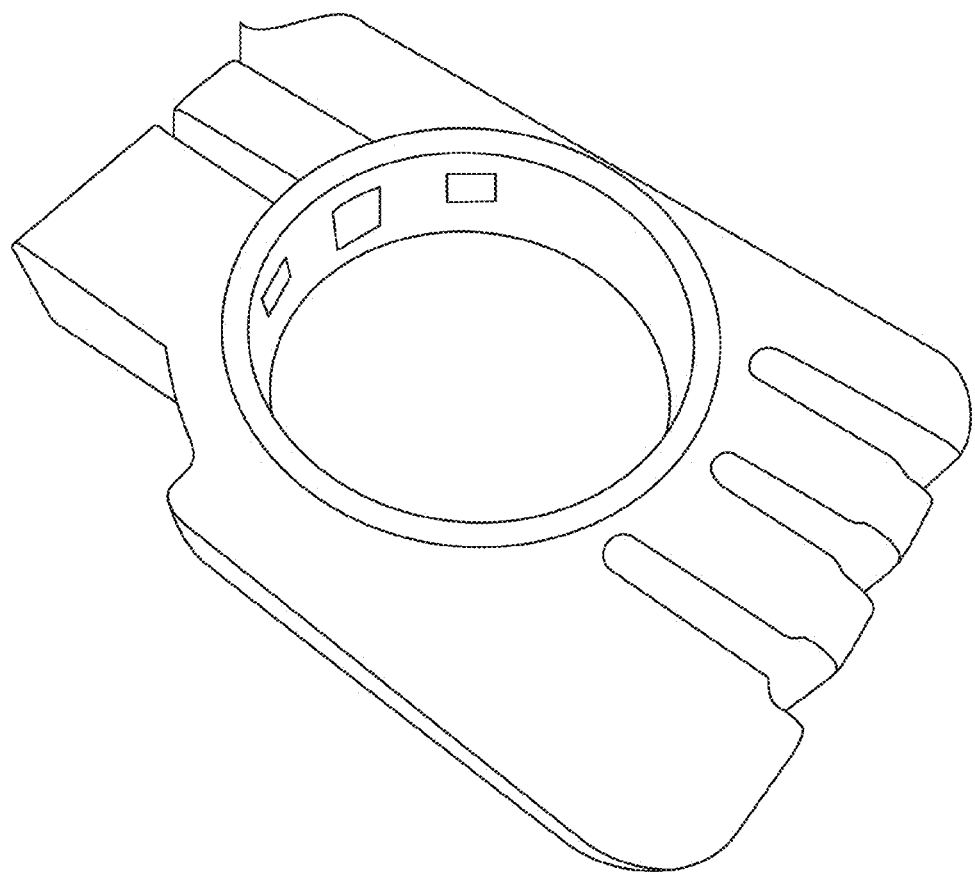
FIG. 6 shows a perspective view of exemplary reagent chambers and syringe channel of the present disclosure.
Figure 7:
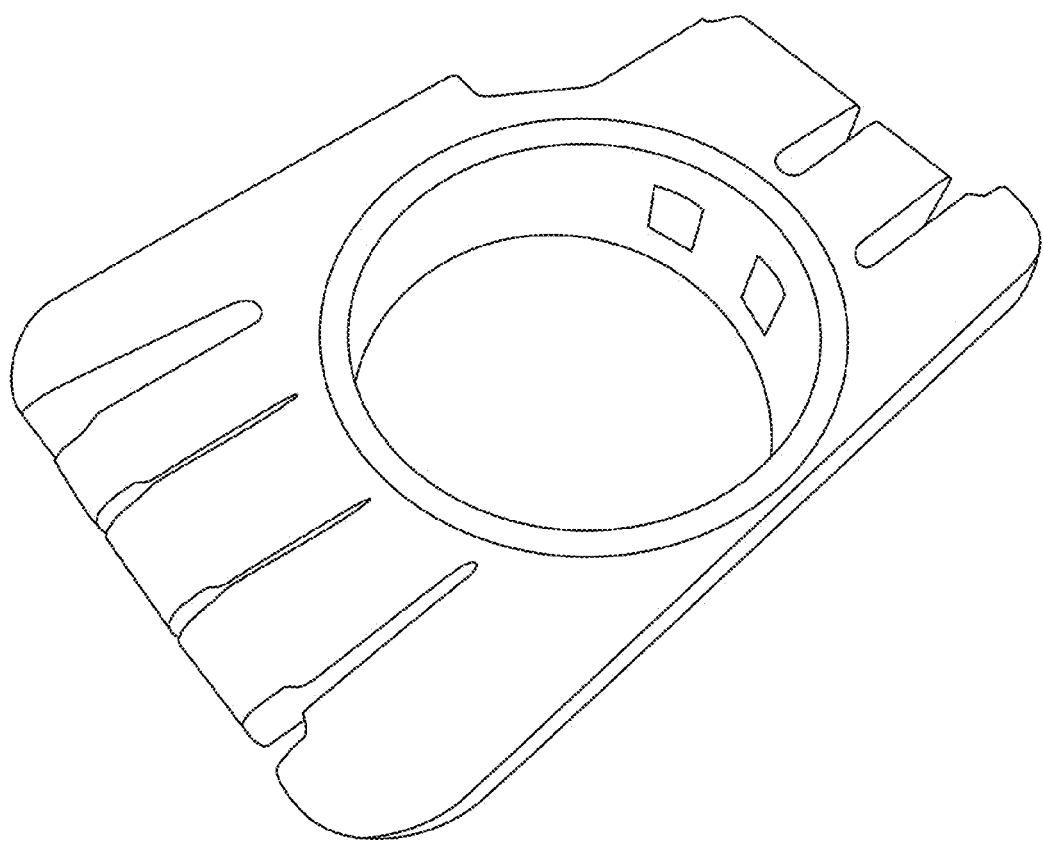
FIG. 7 shows a perspective view of exemplary reagent chambers and syringe channel of the present disclosure.
Figure 8:
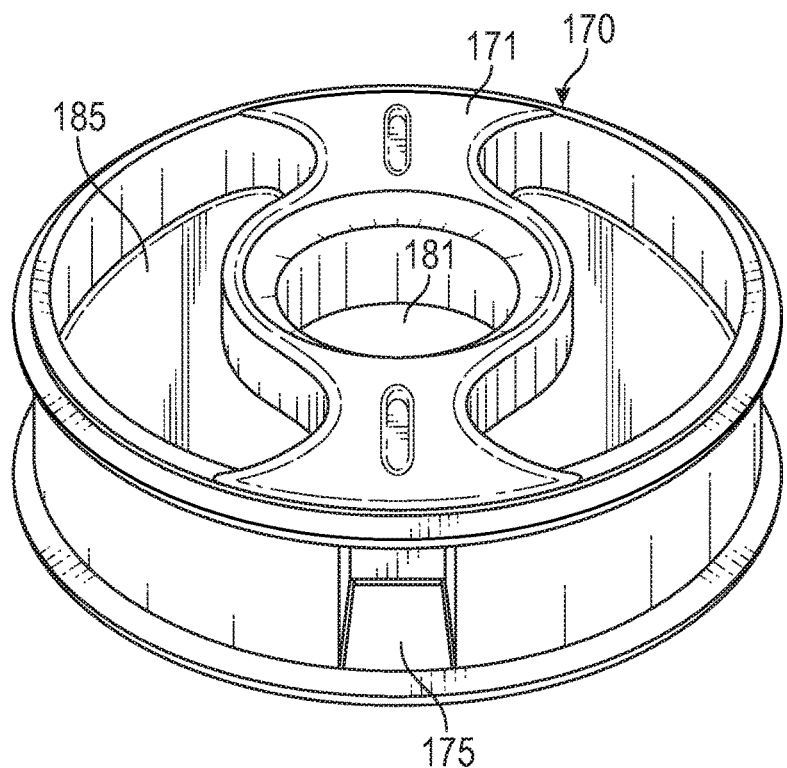
FIG. 8 shows a perspective view of the top side of dial 170 of the present disclosure.
Figure 9:
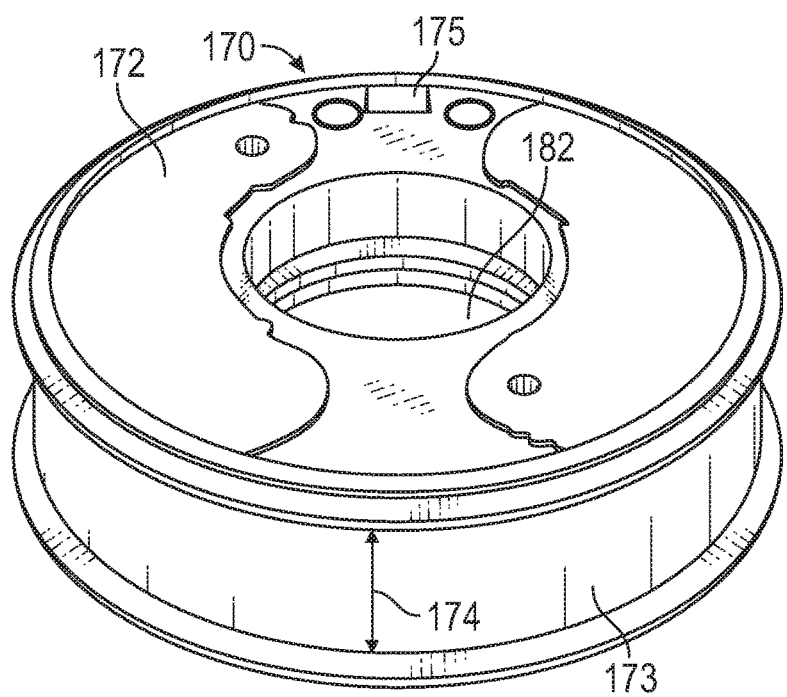
FIG. 9 shows a perspective view of the bottom side of dial 170 of the present disclosure.
Figure 10:
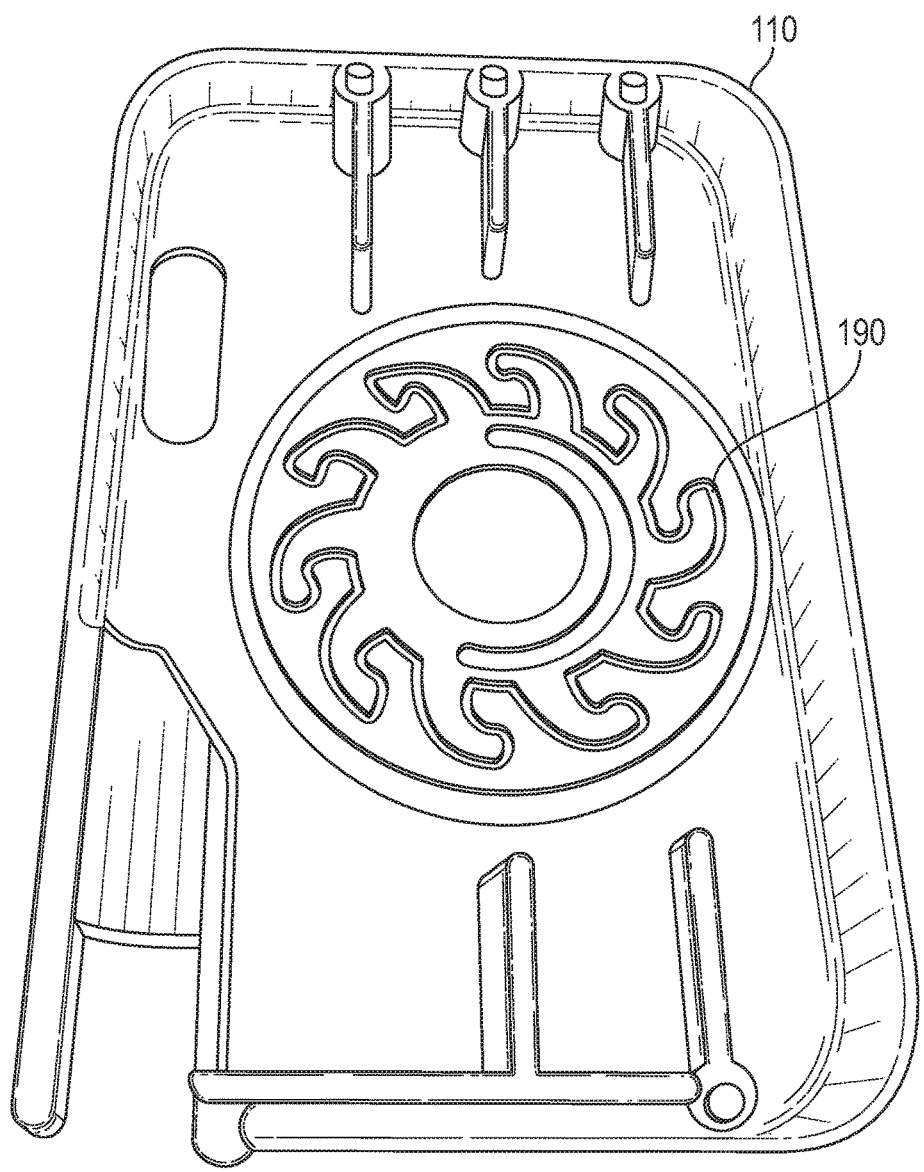
FIG. 10 shows a perspective view of an inside of a bottom cover of an exemplary cartridge featuring a set of grooves from a ratchet mechanism and supports for a four chamber inlay.
Figure 11:
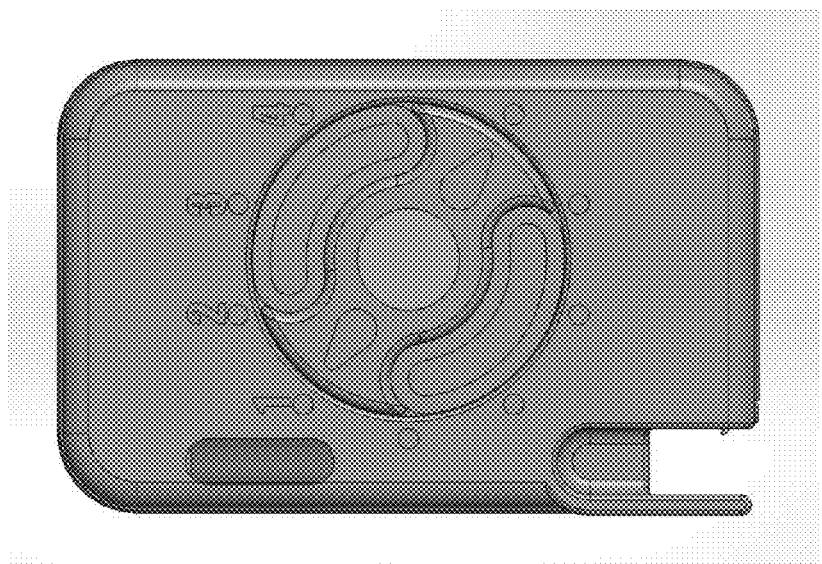
FIG. 11 shows a top view of an exemplary cartridge of the present disclosure.
Figure 12:
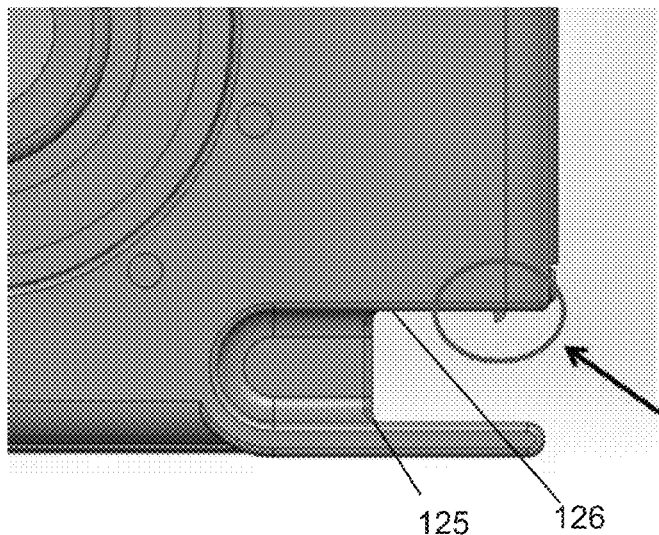
FIG. 12 shows a partial view of syringe lock 129. Syringe lock 129 is a redundant safety feature to prevent an inserted syringe from being removed from the cartridge.
Figure 13:
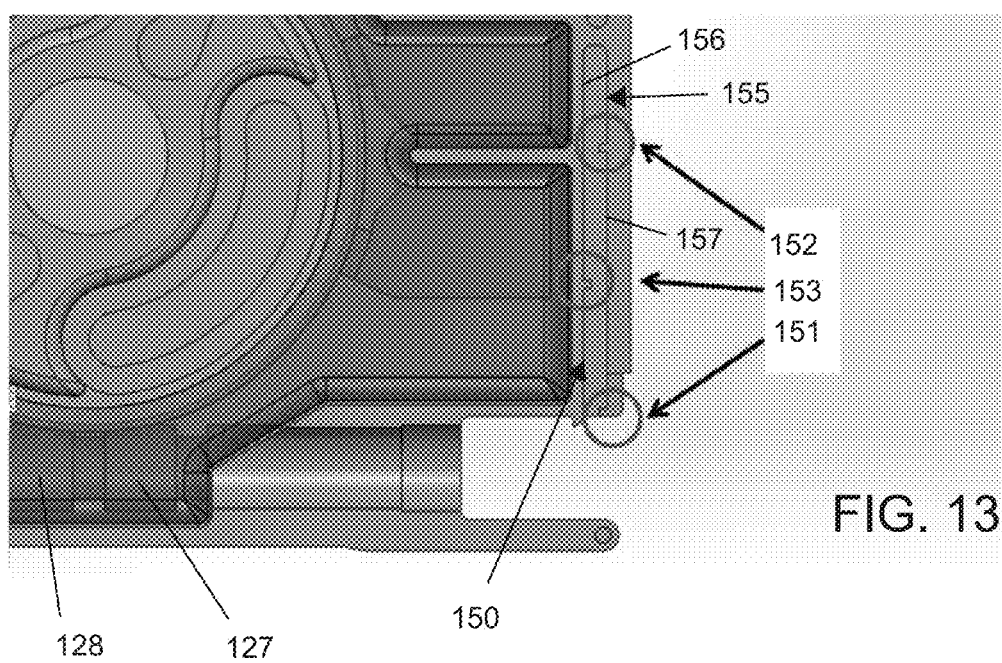
FIG. 13 shows a view of an exemplary locking tab channel. In the present embodiment, three tabs are within the locking tab channel. When the locking tab is fully seated within the locking tab channel in a storage or pre-use position, a second locking tab stop holds the locking tab against the interior slot wall while a tensioning projection provides a counter point of contact that bends that locking tab away from the interior wall. The bend in the locking tab seats its furthest most edge behind a first locking tab stop securely holding the locking tab in place. The locking tab is under continual stress and material selection must be such that it is resistant to stress relaxation—especially given thermal cycling. To engage the locking tab, it must be depressed (pushed toward the interior slot wall) so that it may clear the first locking tab stop. The locking tab can then be slid to the second position to lock the syringe in place. In the locked position, the first locking tab stop presses the tab down toward the interior slot wall while the tensioning projection bends the back of the locking tab away from the interior slot wall. The tensioning projection bends the back of the locking tab such that it seats in front of the second locking tab stop and cannot be slid backward. Thus the locking tab is locked into place.
Figure 14:
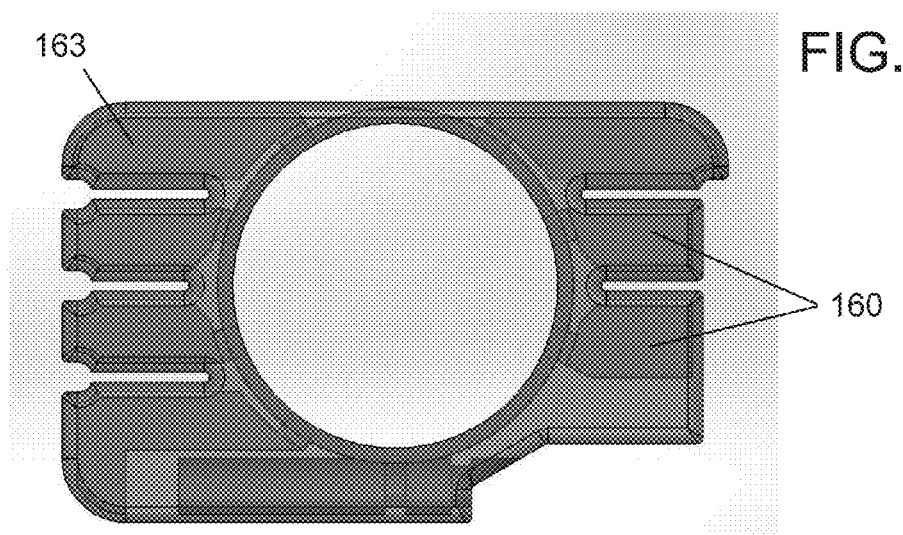
FIG. 14 shows a top view of reagent chambers 160 and 163 and syringe channel 125 of an exemplary embodiment.
Figure 15:
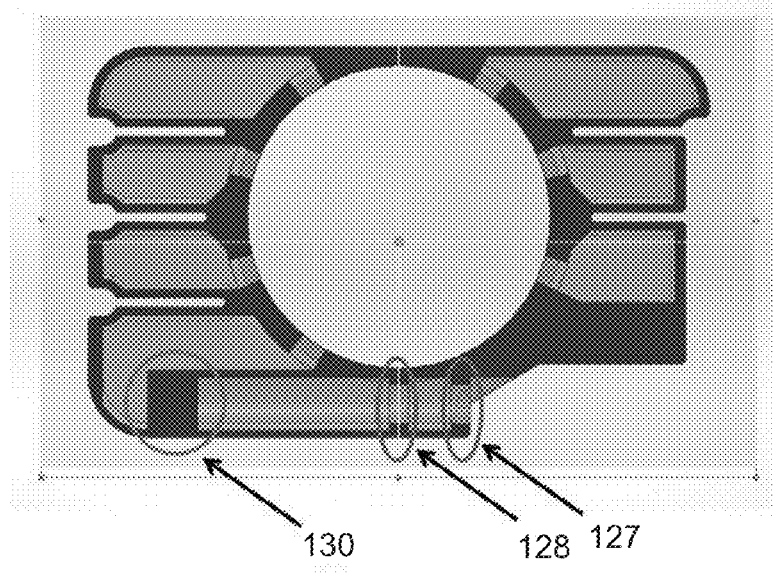
FIG. 15 shows a cross-sectional view of exemplary reagent chambers and syringe channel featuring the syringe based sealing mechanisms including first collar 127, second collar 128, and septum 130. In the illustrated embodiment, first collar 127 and second collar 128 squeeze the body of the inserted syringe to prevent regurgitation of fluids if the sample within the syringe is expelled without puncturing septum 130 or should septum 130 somehow fail. Septum 130 seals around a syringe needle to prevent any leakage.
Figure 16:
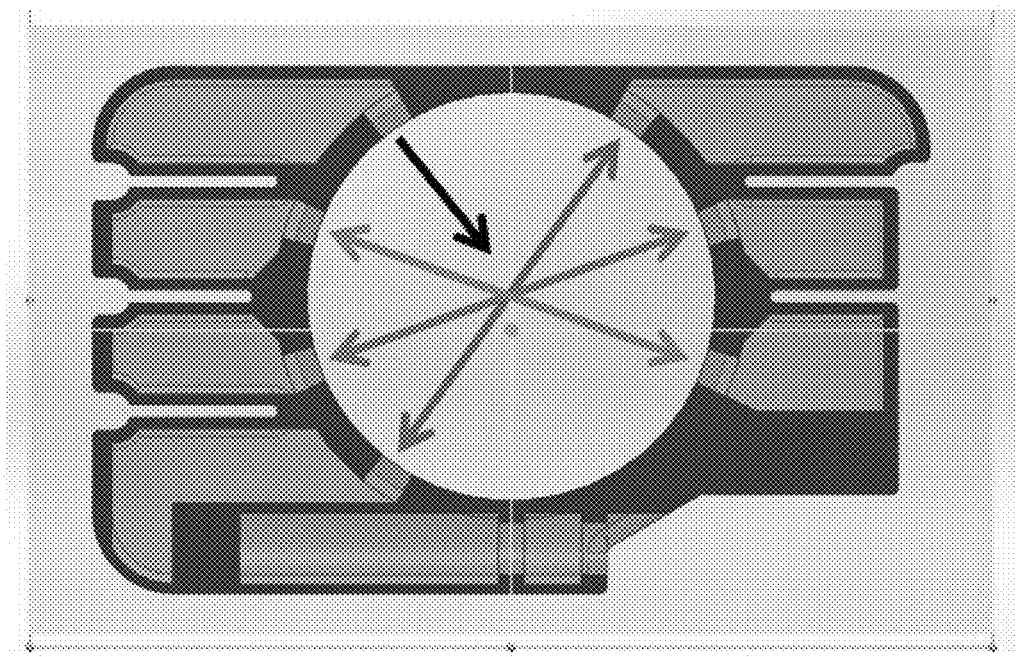
FIG. 16 shows flow paths within an exemplary cartridge without a dial in place. The dial bridges the gap between the paired reagent chambers. The double arrow at the upper and lower most position points to the paired reagent chambers of Stage 1—the capture stage. The double arrow clockwise from Stage 1 points to the paired reagent chambers of Stage 2—the labeling stage. The double arrow clockwise from Stage 2—points to the paired reagent chambers of Stage 3—the wash or rinse stage. The single arrow points away from the final anterior reagent chamber of Stage 4—the measurement stage. During Stage 4, the dial is filled with clean fluid. The dial is now locked in its final position for measurement.
Figure 17:
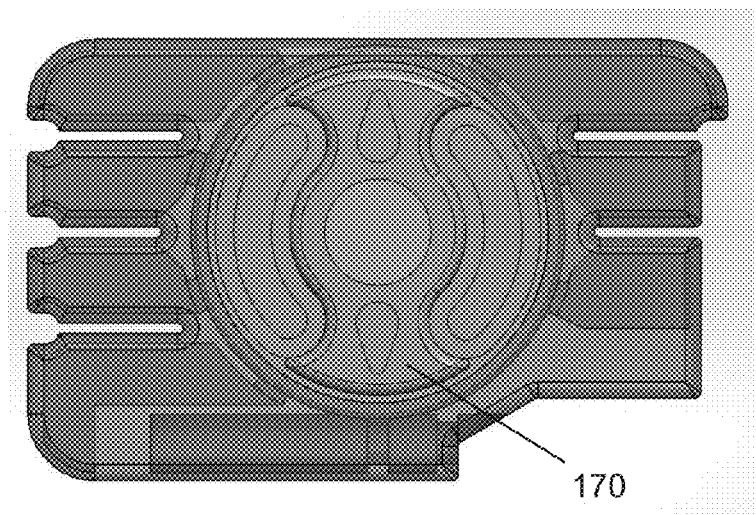
FIG. 17 shows a top view of an exemplary cartridge with dial 170 in place.
Figure 18:
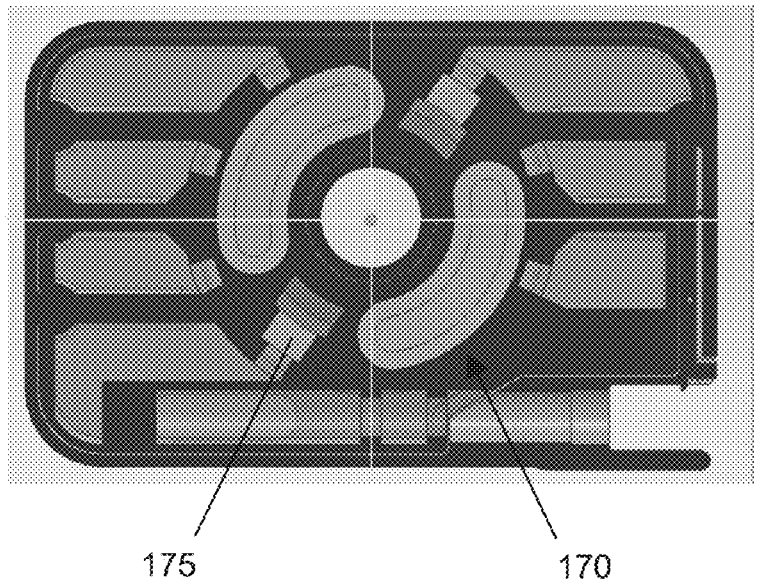
FIG. 18 shows a cross-sectional view of an exemplary cartridge with dial 170 in place featuring dial channel 175. Dial channel 175 bridges the paired reagent chambers.
Figure 20A:
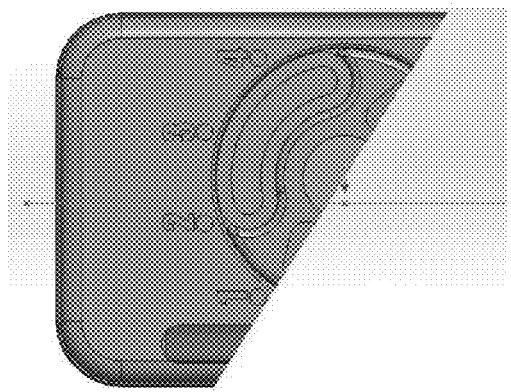
FIG. 20A shows a cross-section taken through Stage 1.
Figure 20B:
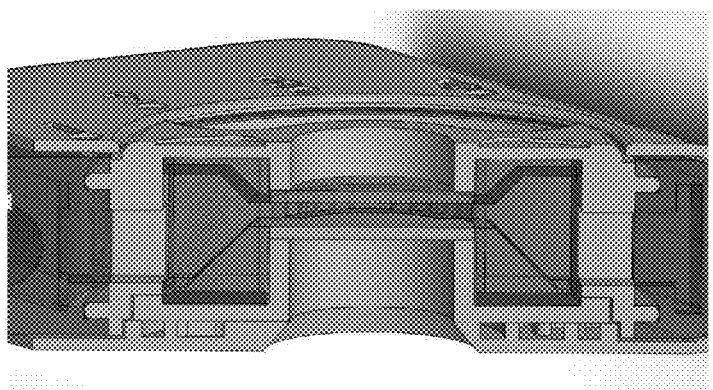
FIG. 20B shows a cross-section of the region of interrogation featuring the dial channel connecting to paired reagent chambers.
Figure 20C:
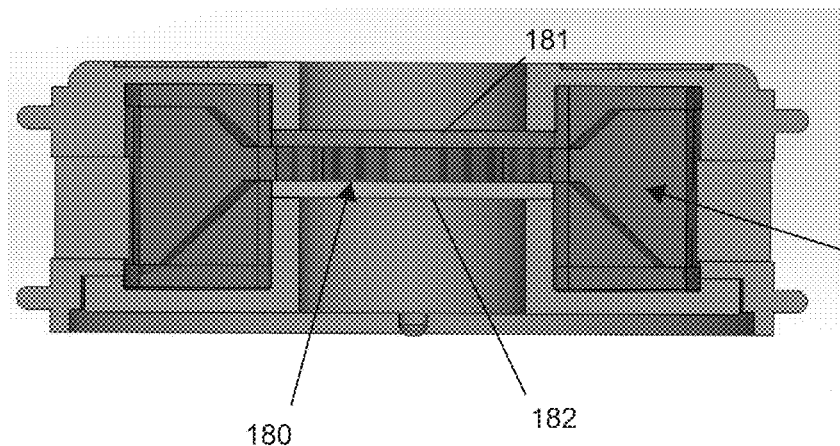
FIG. 20C shows a cross-section of the region of interrogation of the present disclosure featuring the dial channel, the top window, and the bottom window.
Figure 23:
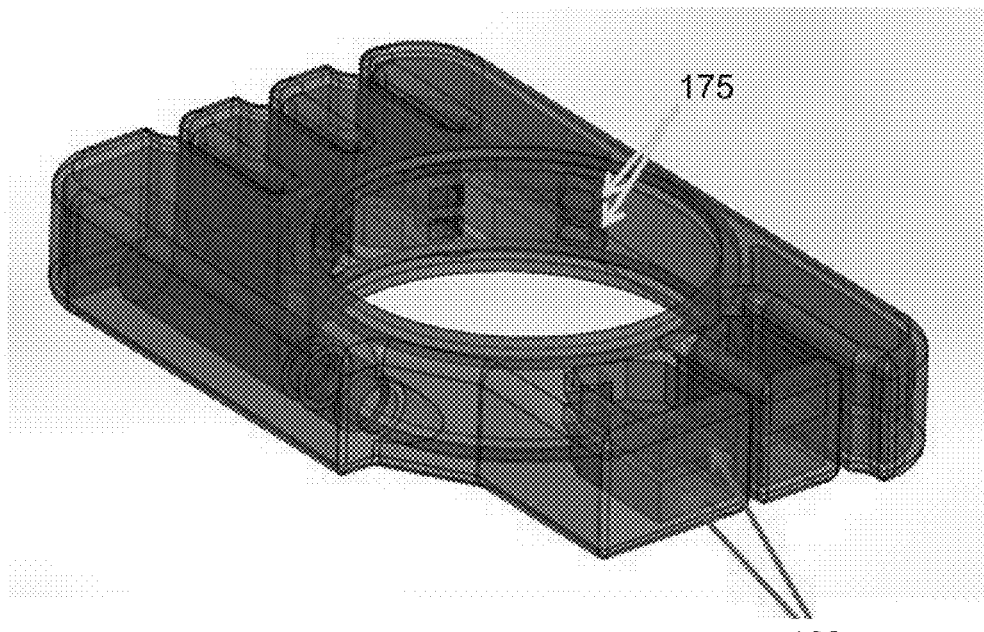
FIG. 23 shows a perspective view of an alternate embodiment of the reagent chambers and the syringe channel of the present disclosure at Stage 2 featuring a double-stacked or bifurcated outer inlay interface with bifurcated dial and central inlay. The inlay is not limited to the depicted configurations. For example, the inlay could potentially consists of a single set of paired reservoirs or a bifurcated/double-stacked version of such a configuration depending on the sample being processed or detection method being used.

Following is a list of elements corresponding to a particular element referred to herein:
- 100 Cartridge-based detection system
- 110 Cartridge
- 111 Cartridge anterior end
- 112 Cartridge posterior end
- 113 Cartridge first side
- 114 Cartridge second side
- 115 Cartridge top surface
- 116 Cartridge bottom surface
- 117 Cartridge thickness
- 120 Syringe port
- 125 Syringe channel
- 126 Syringe channel side wall
- 127 First collar
- 128 Second collar
- 129 Syringe lock
- 130 Septum
- 140 Syringe
- 141 Syringe body
- 145 Needle
- 150 Locking tab
- 151 First locking tab stop
- 152 Second locking tab stop
- 153 Tensioning projection
- 155 Locking tab channel
- 156 Locking tab channel anterior side
- 157 Locking tab channel posterior side
- 160 Reagent chamber
- 161 Anterior reagent chamber
- 162 Posterior reagent chamber
- 163 Final anterior reagent chamber
- 170 Dial
- 171 Dial top surface
- 172 Dial bottom surface
- 173 Dial side wall
- 174 Dial thickness
- 175 Dial channel
- 180 Region of interrogation
- 181 Top window
- 182 Bottom window 185 Dial indentation for fingers
190 Ratchet mechanism
191 Grooved track
192 Pin Referring now to FIGS. 1-24, the present disclosure features a system (100) comprising a cartridge (110) having a plurality of reagent chambers (160) located therein. In some embodiments, each reagent chamber (160) comprises a through-port. In some embodiments, the system (100) comprises a cylindrical dial (170) having a dial channel (175) with an optically transparent region of interrogation (180) centrally located therein. In some embodiments, the dial (170) facilitates a sequential introduction of various fluids contained in the reagent chambers (160) into the sample to be investigated through the dial channel (175). In some embodiments, the system (100) comprises a syringe port (120) located on an outside of the cartridge (110) and fluidly connected to a syringe channel (125) located within the cartridge (110). In some embodiments, an interior end of the syringe channel (125) comprises an injection port.

In some embodiments, the reagent chambers (160) are positioned around the cylindrical dial (170) such that when the cylindrical dial (170) is rotated, the dial channel (175) sequentially aligns with each reagent chamber through-port. In some embodiments, when the reagent chamber through-port aligns with the dial channel (175), a reagent from the reagent chamber can flow into the region of interrogation (180).

In some embodiments, a septum (130) is located on the interior end of the syringe channel (125).

In some embodiments, a first collar (127) is located in the syringe channel (125) next to the syringe port (120). In some embodiments, the first collar (127) is elastomeric.

In some embodiments, a second collar (128) is located in the syringe channel (125) close to the first collar (127). In some embodiments, the second collar (128) is elastomeric.

In some embodiments, a syringe channel volume is greater than a volume of a syringe (140) for safely containing an unintentional discharge from the syringe (140) before piercing the septum (130).

In some embodiments, the dial (170) is centrally located in the cartridge (110). In some embodiments, the dial (170) extends through the cartridge (110) to engage an inside wall of a cartridge bottom surface (116). In some embodiments, the dial (170) comprises a dial thickness (174) from a dial top surface (171) to a dial bottom surface (172) about equal to a cartridge thickness (117), from a cartridge top surface (115) to the cartridge bottom surface (116).

In some embodiments, the dial channel (175) is located through the dial (170) from a first location on a dial side wall (173) to a second location on an opposing side of the dial side wall (173). In some embodiments, the dual window region of interrogation (180) is centrally located in the dial (170). In some embodiments, the dial channel (175) is located between a top window (181) and a bottom window (182) of the dual window region of interrogation (180).

In some embodiments, a cross-section of the dial channel (175) is greater at the first location on the dial side wall (173) and the second location on the dial side wall (173) than a cross-section of the dial channel (175) between the top window (181) and the bottom window (182) of the region of interrogation (180). In some embodiments, a cross-sectional area of the dial channel (175) reduces towards the region of interrogation (180) and increases towards the dial side wall (173) to create bubble inducing turbulence upon agitation of the sample to be investigated.

In some embodiments, a ligand is chemically bound to the region of interrogation (180) on an inside surface of the top window (181) and an inside surface of the bottom window (182) for collecting microbial pathogens or other analytes of interest. In some embodiments, the ligand interacts with the microbial pathogens or other analytes of interest causing them to collect on the inside surface of the top window (181) and the inside surface of the bottom window (182) from the sample to be investigated.

Figure 24:
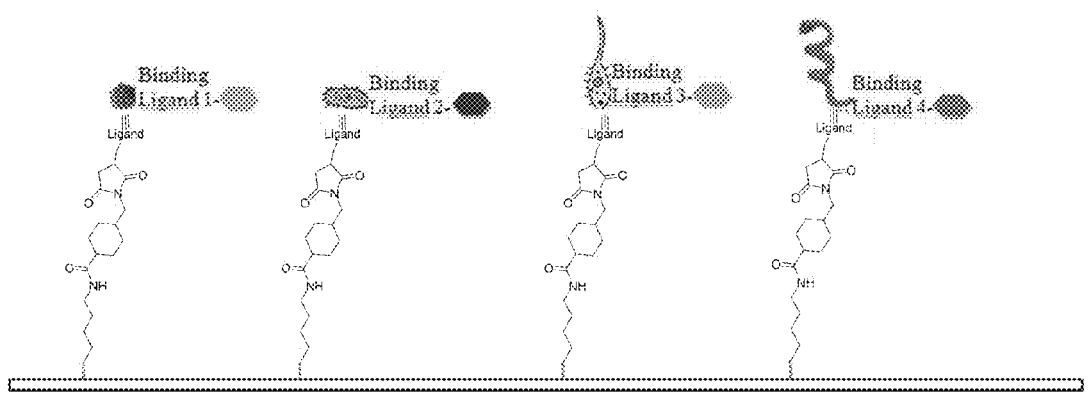
FIG. 24 shows an exemplary design to permit the labeling of as many as 4 different analytes, using 4 different fluorescent dye conjugates.

In some embodiments, the ligand is lignosulfonic acid or heparan sulfate. In some embodiments, a plurality of different ligands may be used. In some embodiments, different ligands may be used, for example, the ligands may be selected from antibodies, protein fragments, peptides, nucleic acids, complex carbohydrates, and organic compounds. For example, FIG. 24 shows an exemplary design to permit the labeling of as many as four different analytes, using four different fluorescent dye conjugates. In some embodiments, one or more different analytes are labeled, such as one, two, three or four different analytes.

In some embodiments, distilled water is located in a reagent chamber (160) for combining with the sample to be investigated and promoting the lysis of human cells (for example, red blood cells) by osmotic shock, thereby releasing any microbial pathogens or other analytes of interest and making them available for capture by the ligand.

In some embodiments, a fluorescence-based molecular tag, such as a fluorescent dye conjugated with another molecule is located in a reagent chamber (160) for combining with the captured sample.

In some embodiments, an agent of chemiluminescence is located in a reagent chamber (160) for combining with the captured sample.

In some embodiments, a lignosulfonic acid-fluorescent dye conjugate is located in a reagent chamber (160) for combining with the captured microbial pathogens or other analytes of interest. In some embodiments, a plurality of types of captured analytes are labeled using a plurality of types of ligand-bound dye conjugates, resulting in the detection of multiple analytes using the multiple dyes and a single detector measurement. In some embodiments, the detector is adapted to measure fluorescence from a plurality of dyes simultaneously. In some embodiments, a plurality of dye conjugates is disposed in a reagent chamber (160) for introduction to the captured analyte sample. In some embodiments, a heat-stable antibody, protein fragment, peptide, nucleic acid, or other compound may be conjugated to the fluorescent dye and located in a reagent chamber (160) for combining with the captured analyte sample, resulting with the captured microbial pathogens or other analytes being labelled with a fluorescent dye. In some embodiments, no fluorescent dye is needed, for example, if the detector is a simple light microscope. In some embodiments, an example of a fluorescent dye is Rhodamine 123.

In some embodiments, a heparan sulfate-fluorescent dye conjugate is located in a reagent chamber (160) for combining with the captured analyte sample resulting with the captured microbial pathogens or other analytes of interest being labelled with fluorescent dye.

In some embodiments, a wash buffer is located in a reagent chamber (160) for combining with the captured analyte sample.

In some embodiments, the reagent chambers (160) comprise a shape of a rectangular prism, triangular prism, hexagonal prism, or pentagonal prism. In some embodiments, the reagent chambers (160) comprise a shape of a cylinder.

In some embodiments, a tapered syringe lock (129) is located on a syringe channel side wall (126) for locking a fully inserted syringe (140) into position.

In some embodiments, a locking tab (150) is slidably located in a locking tab channel (155). In some embodiments, the locking tab channel (155) comprising a locking tab channel anterior side (156) and a locking tab channel posterior side (157) is located on a cartridge posterior end (112). In some embodiments, a first locking tab stop (151) is located on the locking tab channel posterior side (157) next to the syringe port (120) to hold the locking tab into a first, open position. In some embodiments, a second locking tab stop (152) is located on the locking tab channel posterior side (157) at a distance equal to a locking tab length from an opposite syringe channel side wall (126) to hold the locking tab into a second, closed position. In some embodiments, a tensioning projection (153) is located on the locking tab channel anterior side (156) between the first locking tab stop (151) and the second locking tab stop (152) to provide tension on the locking tab (150) in the first position or the second position.

In some embodiments, the dial (170) comprises a first dial indentation (185) and a second dial indentation (185) located on a dial top surface (171) thereon adapted to receive a finger or a thumb of a user inserted therein for manually rotating the dial (170).

In some embodiments, the dial (170) comprises a ratchet mechanism (190) having a grooved track (191) located on a cartridge inside surface and a mated spring-biased pin (192) for following the grooved track (191) located on the dial (170).

In some embodiments, the present disclosure features a cartridge-based detection system (100) to prepare an injected sample to be investigated for determination of a microbial pathogen or another analyte of interest using a detector. In some embodiments, the system (100) comprises a syringe (140) having a needle (145).

In some embodiments, the system (100) comprises a field-safe cartridge (110). In some embodiments, a syringe port (120) is located on the cartridge and a syringe channel (125) is located in the cartridge (110) between a septum (130) and the syringe port (120) and fluidly connected to the syringe port (120). In some embodiments, a first collar (127) is located in the syringe channel (125) next to the syringe port (120). In some embodiments, a second collar (128) is located in the syringe channel (125) close to the first collar (127). In some embodiments, the first collar (127) and the second collar (128) each comprise a diameter smaller than a diameter of the syringe channel (125) for sealing against a syringe body (141) upon insertion of the syringe (140). In some embodiments, a syringe channel volume is greater than a volume of the syringe (140) for safely containing an unintentional discharge from the syringe (140) before piercing the septum (130).

In some embodiments, the system (100) comprises a plurality of reagent chambers (160) located in the cartridge (110) comprising a first anterior reagent chamber (161), a first posterior reagent chamber (162), a plurality of additional sequentially mated anterior reagent chambers (161) and opposing posterior reagent chambers (162), and a final anterior reagent chamber (163). In some embodiments, the first anterior reagent chamber (161) is next to the septum (130).

In some embodiments, the system (100) comprises a rotating cylindrical dial (170) having a dial channel (175) located there through. In some embodiments, the dial (170) facilitates a sequential introduction of various fluids contained in the reagent chambers (160) into the sample to be investigated through the dial channel (175). In some embodiments, the dial (170) is centrally located in the cartridge (110). In some embodiments, the dial (170) comprises a dial top surface (171), a dial bottom surface (172), and a cylindrical dial side wall (173). In some embodiments, the dial (170) extends through the cartridge (110) to engage an inside wall of the cartridge bottom surface (116). In some embodiments, the dial (170) comprises a dial thickness (174) from the dial top surface (171) to the dial bottom surface (172) about equal to the cartridge thickness (117). In some embodiments, the dial channel (175) is located through the dial (170) from a first location on the dial side wall (173) to a second location on an opposing side of the dial side wall (173). In some embodiments, a dual window region of interrogation (180) is centrally located in the dial (170). In some embodiments, the dual window region of interrogation (180) is optically transparent but can be a region that is transparent for other kinds of measurements, e.g. x-ray, magnetic, radio waves, etc. In some embodiments, the dial channel (175) is located between a top window (181) and a bottom window (182) of the dual window region of interrogation (180). In some embodiments, a cross-section of the dial channel (175) is greater at the first location on the dial side wall (173) and the second location on the dial side wall (173) than the cross-section of the dial channel (175) between the top window (181) and the bottom window (182) of the region of interrogation (180). In some embodiments, a cross-sectional area of the dial channel (175) reduces towards the region of interrogation (180) and increases towards the dial side wall (173) to create bubble inducing turbulence upon agitation of the sample to be investigated. In some embodiments, when the dial (170) is rotated into a position marked on the top of the cartridge, each mated anterior reagent chamber (161) and posterior reagent chamber (162) are fluidly connected via the dial channel (175), In some embodiments, ligands are located in the region of interrogation (180) on an inside surface of the top window (181) and an inside surface of the bottom window (182) for collecting microbial pathogens or other analytes of interest. In some embodiments, the ligand interacts with the microbial pathogens or other analytes of interest causing them to collect on the inside surface of the top window (181) and the inside surface of the bottom window (182) from the sample to be investigated.

In some embodiments, the ligand is lignosulfonic acid or heparan sulfate.

In some embodiments, distilled water is located in a reagent chamber (160) for combining with the sample to be investigated.

In some embodiments, fluorescence-based dye reagents are located in a reagent chamber (160) for combining with the sample to be investigated.

In some embodiments, chemiluminescence based reagents are located in a reagent chamber (160) for combining with the sample to be investigated.

In some embodiments, a lignosulfonic acid-fluorescent dye conjugate is located in a reagent chamber (160) for combining with the sample to be investigated resulting with the captured microbial pathogens or other analytes of interest being labelled with that fluorescent dye.

In some embodiments, a heparan sulfate-fluorescent dye conjugate is located in a reagent chamber (160) for combining with the sample to be investigated resulting with the captured microbial pathogens or other analytes of interest being labelled with that fluorescent dye.

In some embodiments, a wash buffer is located in a reagent chamber (160) for combining with the sample to be investigated.

In some embodiments, the reagent chambers (160) comprise a shape of a rectangular prism, triangular prism, hexagonal prism, or pentagonal prism. In some embodiments, the reagent chambers (160) comprise a shape of a cylinder.

In some embodiments, a tapered syringe lock (129) is located on a syringe channel side wall (126) for locking a fully inserted syringe (140) into position.

In some embodiments, a locking tab (150) is slidably located in a locking tab channel (155). In some embodiments, the locking tab channel (155) comprising a locking tab channel anterior side (156) and a locking tab channel posterior side (157) is located on the cartridge posterior end (112). In some embodiments, a first locking tab stop (151) is located on the locking tab channel posterior side (157) next to the syringe port (120) to hold the locking tab into a first, open position. In some embodiments, a second locking tab stop (152) is located on the locking tab channel posterior side (157) at a distance equal to a locking tab length from an opposite syringe channel side wall (126) to hold the locking tab into a second, closed position. In some embodiments, a tensioning projection (153) is located on the locking tab channel anterior side (156) between the first locking tab stop (151) and the second locking tab stop (152) to provide tension on the locking tab (150) in the first position or the second position.

In some embodiments, the dial (170) comprises a first dial indentation (185) and a second dial indentation (185) adapted to receive a finger or a thumb of a user inserted therein for manually rotating the dial (170).

In some embodiments, the dial (170) comprises a ratchet mechanism (190) having a grooved track (191) located on a cartridge inside surface and a mated spring-biased pin (192) for following the grooved track (191) located on the dial (170).

In some embodiments, the present disclosure features a disposable cartridge-based detection system (100) to prepare an injected sample to be investigated for determination of a microbial pathogen or another analyte of interest using a detector. In some embodiments, the system (100) comprises a syringe (140) having a needle (145).

In some embodiments, the system (100) comprises a field-safe, hollow cartridge (110) having a cartridge anterior end (111), a cartridge posterior end (112), a cartridge first side (113), a cartridge second side (114), a cartridge top surface (115), and a cartridge bottom surface (116). In some embodiments, the cartridge (110) comprises a cartridge thickness (117) between the cartridge top surface (115) and the cartridge bottom surface (116).

In some embodiments, a syringe port (120) is located on the cartridge posterior end (112) close to the cartridge first side (113). In some embodiments, a cylindrical syringe channel (125) is located in the cartridge (110) between a septum (130) and the syringe port (120) and is fluidly connected to the syringe port (120). In some embodiments, an elastomeric first collar (127) is located in the syringe channel (125) next to the syringe port (120). In some embodiments, an elastomeric second collar (128) is located in the syringe channel (125) close to the first collar (127). In some embodiments, the first collar (127) and the second collar (128) each comprise a diameter smaller than a diameter of the syringe channel (125) for sealing against a syringe body (141) upon insertion of the syringe (140). In some embodiments, a syringe channel volume is greater than a volume of the syringe (140) for safely containing an unintentional discharge from the syringe (140) before piercing the septum (130).

In some embodiments, a tapered syringe lock (129) is located on a syringe channel side wall (126) for locking a fully inserted syringe (140) into position. In some embodiments, a locking tab (150) is slidably located in a locking tab channel (155). In some embodiments, the locking tab channel (155) comprising a locking tab channel anterior side (156) and a locking tab channel posterior side (157) is located on the cartridge posterior end (112). In some embodiments, a first locking tab stop (151) is located on the locking tab channel posterior side (157) next to the syringe port (120) to hold the locking tab into a first, open position. In some embodiments, a second locking tab stop (152) is located on the locking tab channel posterior side (157) at a distance equal to a locking tab length from an opposite syringe channel side wall (126) to hold the locking tab into a second, closed position. In some embodiments, a tensioning projection (153) is located on the locking tab channel anterior side (156) between the first locking tab stop (151) and the second locking tab stop (152) to provide tension on the locking tab (150) in the first position or the second position.

In some embodiments, the system (100) comprises a plurality of reagent chambers (160) located in the cartridge (110) comprising a first anterior reagent chamber (161), a first posterior reagent chamber (162), a plurality of additional sequentially mated anterior reagent chambers (161) and opposing posterior reagent chambers (162), and a final anterior reagent chamber (163). In some embodiments, the first anterior reagent chamber (161) is next to the septum (130).

In some embodiments, the system (100) comprises a rotating cylindrical dial (170) having a dial channel (175) located there through. In some embodiments, the dial (170) facilitates a sequential introduction of various fluids contained in the reagent chambers (160) into the sample to be investigated through the dial channel (175). In some embodiments, the dial (170) is centrally located in the cartridge (110). In some embodiments, the dial (170) comprises a dial top surface (171), a dial bottom surface (172), and a cylindrical dial side wall (173). In some embodiments, the dial (170) extends through the cartridge (110) to engage an inside wall of the cartridge bottom surface (116). In some embodiments, the dial (170) comprises a dial thickness (174) from the dial top surface (171) to the dial bottom surface (172) about equal to the cartridge thickness (117).

In some embodiments, the dial channel (175) is located through the dial (170) from a first location on the dial side wall (173) to a second location on an opposing side of the dial side wall (173). In some embodiments, a dual window region of interrogation (180) is centrally located in the dial (170). In some embodiments, the dual window region of interrogation (180) is optically transparent but can be a region that is transparent for other kinds of measurements, e.g. x-ray, magnetic, radio waves, etc. In some embodiments, the dial channel (175) is located between a top window (181) and a bottom window (182) of the dual window region of interrogation (180). In some embodiments, a cross-section of the dial channel (175) is greater at the first location on the dial side wall (173) and the second location on the dial side wall (173) than the cross-section of the dial channel (175) between the top window (181) and the bottom window (182) of the region of interrogation (180). In some embodiments, a cross-sectional area of the dial channel (175) reduces towards the region of interrogation (180)

and increases towards the dial side wall (173) to induce bubbles upon agitation of the sample to be investigated. In some embodiments, when the dial (170) is rotated into a position, each mated anterior reagent chamber (161) and posterior reagent chamber (162) are fluidly connected via the dial channel (175).

In some embodiments, the dial (170) comprises a first dial indentation (185) and a second dial indentation (185) adapted to receive a finger or a thumb of a user inserted therein for manually rotating the dial (170). In some embodiments, the dial (170) comprises a ratchet mechanism (190) having a grooved track (191) located on a cartridge inside surface and a mated spring-biased pin (192) for following the grooved track (191).

In some embodiments, for placement of the dial (170) to a first position, the dial (170) is rotated in a clockwise manner. In some embodiments, the dial (170) encounters a first front stop. In some embodiments, the dial channel (175) is fluidly connected to and in alignment with the first anterior reagent chamber (161) and the first posterior reagent chamber (162).

In some embodiments, for placement of the dial (170) in a next position, the dial (170) is rotated in a counter clockwise manner to release the dial (170) from the first front stop. In some embodiments, the dial (170) encounters a first back stop. In some embodiments, the dial is rotated in a clockwise manner. In some embodiments, the dial (170) encounters a next front stop. In some embodiments, the dial channel (175) is fluidly connected to and in alignment with the next anterior reagent chamber (161) and the next posterior reagent chamber (162).

In some embodiments, for placement of the dial (170) in a final position, the dial (170) is rotated in a counter clockwise manner to release the dial (170) from the next front stop. In some embodiments, the dial (170) encounters a final back stop. In some embodiments, the dial is rotated in a clockwise manner. In some embodiments, the dial (170) encounters a final front stop. In some embodiments, the dial channel (175) is fluidly connected to and in alignment with the final anterior reagent chamber (161). In some embodiments, upon reaching the final position, the dial (170) is prevented from rotation to a prior position.

In some embodiments, a user draws a sample to be investigated into the syringe (140). In some embodiments, the user inserts the syringe (140) into the syringe channel (125). In some embodiments, the syringe body (141) slides through the first collar (127) and the second collar (128). In some embodiments, the first collar (127) and the second collar (128) snuggly and sealably hold the syringe (140) into the syringe channel (125). In some embodiments, the syringe needle (145) pierces the septum (130). In some embodiments, a syringe back edge slides past the syringe lock (129) until the syringe lock (129) can snap over the syringe back edge affixing it into position. In some embodiments, the user activates the syringe (140) dispensing the sample to be investigated into the first anterior reagent chamber (161). In some embodiments, the locking tab (150) is depressed toward the cartridge (110) to release it from the first locking tab stop (151). In some embodiments, the locking tab (150) is slidably moved to the second position to cover the syringe (140) and the syringe channel (125) to block the syringe (140) from removal. In some embodiments, the second locking tab stop (152) prevents the locking tab (150) from sliding back to the first position via tension from the tensioning projection (153). In some embodiments, the dial (170) is moved to a first position. In some embodiments, the device is shaken or rocked to flush the fluid across the region of interrogation (180) between the first anterior reagent chamber (161) and the first posterior reagent chamber (162). In some embodiments, upon shaking or rocking, bubbles are formed and passed through the dial channel (175), causing the microbial pathogens or other analytes of interest to be transported in close proximity to inside surfaces of the region of interrogation (180) via creation of a thin film on the inside surfaces due to bubble flow through the dial channel (175). In some embodiments, the microbial pathogens or other analytes of interest are retained against the inside surfaces of the region of interrogation (180) of the dial channel (175). In some embodiments, the fluid is drained into the posterior reagent chamber before rotating the dial to the next set of reagent chambers. In some embodiments, the dial (170) is moved to a next, sequential position. In some embodiments, the device is shaken or rocked to flush the fluid across the region of interrogation (180) between the next anterior reagent chamber (161) and the next posterior reagent chamber (162). In some embodiments, upon shaking or rocking, bubbles are formed and passed through the dial channel (175), causing the ligand-dye conjugates to be transported in close proximity to inside surfaces of the region of interrogation (180) via creation of a thin film on the inside surfaces due to bubble flow through the dial channel (175). In some embodiments, the ligand-dye conjugates are bound to the microbial pathogens or other analytes of interest on the surfaces of the region of interrogation (180) of the dial channel (175). In some embodiments, the fluid is drained into the posterior reagent chamber before rotating the dial to the next set of reagent chambers. In some embodiments, the excess ligand-dye conjugates not bound to the microbial pathogens and analytes is removed by rinsing with a buffer solution or distilled water. In some embodiments, this fluid is drained into the posterior reagent chamber before rotating the dial (170) to the final reagent chamber (163) and the dial (170) is locked into position and prevented from rotation to a prior position. In some embodiments, the disposable cartridge-based detection system (100) prepares an injected sample to be investigated for determination of a microbial pathogen or another analyte of interest using a detector.

In some embodiments, a ligand is located in the region of interrogation (180) on an inside surface of the top window (181) and an inside surface of the bottom window (182) for collecting microbial pathogens or other analytes of interest. In some embodiments, the ligand interacts with the microbial pathogens or other analytes of interest causing them to collect on the inside surface of the top window (181) and the inside surface of the bottom window (182) from the sample to be investigated.

In some embodiments, the ligand is lignosulfonic acid or heparan sulfate.

In some embodiments, distilled water or buffer is located in a reagent chamber (160) for combining with the sample to be investigated.

In some embodiments, ligand-bound fluorescence dyes are located in a reagent chamber (160) for combining with the bound microbial pathogens or other analyte-bound sample.

In some embodiments, ligand-bound chemiluminescent dyes are located in a reagent chamber (160) for combining with the bound microbial pathogen or other analyte sample.

In some embodiments, a lignosulfonic acid-fluorescent dye conjugate is located in a reagent chamber (160) for combining with the bound sample resulting with the captured microbial pathogens or other analytes of interest being labelled with that specific fluorescent dye.

In some embodiments, a heparan sulfate-fluorescent dye conjugate is located in a reagent chamber (160) for combining with the bound sample resulting with the captured microbial pathogens or other analytes of interest being labelled with that specific fluorescent dye.

In some embodiments, a wash buffer is located in a reagent chamber (160) for combining with the sample to be investigated.

In some embodiments, the reagent chambers (160) comprise a shape of a rectangular prism, triangular prism, hexagonal prism, pentagonal prism, or trapezoidal prism or a combination thereof.

In some embodiments, the reagent chambers (160) comprise a shape of a cylinder.

In some embodiments, the present disclosure features a method for preparing an injected sample to be investigated for determination of a microbial pathogen or another analyte of interest using a detector. In some embodiments, the method comprises obtaining a disposable cartridge-based detection system (100) to prepare an injected sample to be investigated for determination of a microbial pathogen or another analyte of interest using a detector. In some embodiments, the system (100) comprises a syringe (140) having a needle (145). a field-safe, hollow cartridge (110) having a cartridge anterior end (111), a cartridge posterior end (112), a cartridge first side (113), a cartridge second side (114), a cartridge top surface (115), and a cartridge bottom surface (116). In some embodiments, the cartridge (110) comprises a cartridge thickness (117) between the cartridge top surface (115) and the cartridge bottom surface (116). In some embodiments, a syringe port (120) is located on the cartridge posterior end (112) close to the cartridge first side (113). In some embodiments, a cylindrical syringe channel (125) is located in the cartridge (110) between a septum (130) and the syringe port (120) and fluidly connected to the syringe port (120). In some embodiments, an elastomeric first collar (127) is located in the syringe channel (125) next to the syringe port (120). In some embodiments, an elastomeric second collar (128) is located in the syringe channel (125) close to the first collar (127). In some embodiments, the first collar (127) and the second collar (128) each comprise a diameter smaller than a diameter of the syringe channel (125) for sealing against a syringe body (141) upon insertion of the syringe (140). In some embodiments, a syringe channel volume is greater than a volume of the syringe (140) for safely containing an unintentional discharge from the syringe (140) before piercing the septum (130). In some embodiments, a tapered syringe lock (129) is located on a syringe channel side wall (126) for locking a fully inserted syringe (140) into position. In some embodiments, a locking tab (150) is slidably located in a locking tab channel (155). In some embodiments, the locking tab channel (155) comprising a locking tab channel anterior side (156) and a locking tab channel posterior side (157) is located on the cartridge posterior end (112). In some embodiments, a first locking tab stop (151) is located on the locking tab channel posterior side (157) next to the syringe port (120) to hold the locking tab into a first, open position. In some embodiments, a second locking tab stop (152) is located on the locking tab channel posterior side (157) at a distance equal to a locking tab length from an opposite syringe channel side wall (126) to hold the locking tab into a second, closed position. In some embodiments, a tensioning projection (153) is located on the locking tab channel anterior side (156) between the first locking tab stop (151) and the second locking tab stop (152) to provide tension on the locking tab (150) in the first position or the second position. a plurality of reagent chambers (160) located in the cartridge (110) comprising a first anterior reagent chamber (161), a first posterior reagent chamber (162), a plurality of additional sequentially mated anterior reagent chambers (161) and opposing posterior reagent chambers (162), and a final anterior reagent chamber (163). In some embodiments, the first anterior reagent chamber (161) is next to the septum (130). and a rotatable cylindrical dial (170) having a dial channel (175) located there through. In some embodiments, the dial (170) facilitates a sequential introduction of various fluids contained in the reagent chambers (160) into the sample to be investigated through the dial channel (175). In some embodiments, the dial (170) is centrally located in the cartridge (110). In some embodiments, the dial (170) comprises a dial top surface (171), a dial bottom surface (172), and a cylindrical dial side wall (173). In some embodiments, the dial (170) extends through the cartridge (110) to engage an inside wall of the cartridge bottom surface (116). In some embodiments, the dial (170) comprises a dial thickness (174) from the dial top surface (171) to the dial bottom surface (172) about equal to the cartridge thickness (117). In some embodiments, the dial channel (175) is located through the dial (170) from a first location on the dial side wall (173) to a second location on an opposing side of the dial side wall (173). In some embodiments, a dual window region of interrogation (180) is centrally located in the dial (170). In some embodiments, the dual window region of interrogation (180) is optically transparent but can be a region that is transparent for other kinds of measurements, e.g. x-ray, magnetic, radio waves, etc. In some embodiments, the dial channel (175) is located between a top window (181) and a bottom window (182) of the dual window region of interrogation (180). In some embodiments, a cross-section of the dial channel (175) is greater at the first location on the dial side wall (173) and the second location on the dial side wall (173) than the cross-section of the dial channel (175) between the top window (181) and the bottom window (182) of the region of interrogation (180). In some embodiments, a cross-sectional area of the dial channel (175) reduces towards the region of interrogation (180) and increases towards the dial side wall (173) to create bubbles upon agitation of the sample to be investigated. In some embodiments, when the dial (170) is rotated into a position, each mated anterior reagent chamber (161) and posterior reagent chamber (162) are fluidly connected via the dial channel (175). In some embodiments, the dial (170) comprises a first dial indentation (185) and a second dial indentation (185) adapted to receive a finger or a thumb of a user inserted therein for manually rotating the dial (170). In some embodiments, the dial (170) comprises a ratchet mechanism (190) having a grooved track (191) located on a cartridge inside surface and a mated spring-biased pin (192) for following the grooved track (191). In some embodiments, for placement of the dial (170) to a first position, the dial (170) is rotated in a clockwise manner. In some embodiments, the dial (170) encounters a first front stop. In some embodiments, the dial channel (175) is fluidly connected to and in alignment with the first anterior reagent chamber (161) and the first posterior reagent chamber (162). In some embodiments, for placement of the dial (170) in a next position, the dial (170) is rotated in a counter clockwise manner to release the dial (170) from the first front stop. In some embodiments, the dial (170) encounters a first back stop. In some embodiments, the dial is rotated in a clockwise manner. In some embodiments, the dial (170) encounters a next front stop. In some embodiments, the dial channel (175) is fluidly connected to and in alignment with the next anterior reagent chamber (161) and the next posterior reagent chamber (162). In some embodiments, for placement of the dial (170) in a final position, the dial (170) is rotated in a counter clockwise manner to release the dial (170) from the next front stop. In some embodiments, the dial (170) encounters a final back stop. In some embodiments, the dial is rotated in a clockwise manner. In some embodiments, the dial (170) encounters a final front stop. In some embodiments, the dial channel (175) is fluidly connected to and in alignment with the final anterior reagent chamber (161). In some embodiments, upon reaching the final position, the dial (170) is prevented from rotation to a prior position. In some embodiments, each chamber comprises a reagent located therein.

In some embodiments, the method comprises drawing a sample to be investigated into the syringe (140).

In some embodiments, the method comprises inserting the syringe (140) into the syringe channel (125). In some embodiments, the syringe body (141) slides through the first collar (127) and the second collar (128). In some embodiments, the first collar (127) and the second collar (128) snuggly and sealably hold the syringe (140) into the syringe channel (125). In some embodiments, the syringe needle (145) pierces the septum (130). In some embodiments, a syringe back edge slides past the syringe lock (129) until the syringe lock (129) snaps over the syringe back edge affixing it into position.

In some embodiments, the method comprises activating the syringe (140) dispensing the sample to be investigated into the first anterior reagent chamber (161).

In some embodiments, the method comprises depressing the locking tab (150) toward the cartridge (110) to release it from the first locking tab stop (151). In some embodiments, the locking tab (150) is slidably moved to the second position to cover the syringe (140) and the syringe channel (125) to block the syringe (140) from removal. In some embodiments, the second locking tab stop (152) prevents the locking tab (150) from sliding back to the first position via tension from the tensioning projection (153).

In some embodiments, the method comprises moving the dial (170) to a first position. In some embodiments, the device is shaken or rocked to flush the fluid across the region of interrogation (180) between the first anterior reagent chamber (161) and the first posterior reagent chamber (162). In some embodiments, upon shaking or rocking, bubbles are formed and passed through the dial channel (175), causing the microbial pathogens and analytes of interest to be transported in close proximity to inside surfaces of the region of interrogation (180) via creating a thin film on the inside surfaces due to bubble flow through the dial channel (175). In some embodiments, the microbial pathogens and other analytes of interest are retained against the inside surfaces of the region of interrogation (180) of the dial channel (175).

In some embodiments, the method comprises moving the dial (170) to a next, sequential position. In some embodiments, the device is agitated to flush the fluid across the region of interrogation (180) between the next anterior reagent chamber (161) and the next posterior reagent chamber (162). In some embodiments, upon shaking, bubbles are formed and passed through the dial channel (175), causing the ligand-fluorescent dye conjugate to be bound to the sample due to bubble flow through the dial channel (175) resulting in the microbial pathogens or other analytes of interest being labelled with that specific fluorescent dye. In some embodiments, the microbial pathogens and analytes of interest are retained against the inside surfaces of the region of interrogation (180) of the dial channel (175).

In some embodiments, the method comprises repeating the process until the dial (170) is moved into a final position. In some embodiments, the sample to be investigated is sealed into the final anterior reagent chamber (163) and the dial (170) is locked into position and prevented from rotation to a prior position.

In some embodiments, the method comprises analyzing the sample to be investigated through the region of interrogation (180) using visual indication, magnifying equipment, and/or illuminating equipment.

In some embodiments, the disposable cartridge-based detection system (100) prepares an injected sample to be investigated for determination of a microbial pathogen or another analyte of interest using a detector.

In some embodiments, novel features of the present disclosure include component modularity. In some embodiments, novel features of the present disclosure include a reusable outer shell. In some embodiments, novel features of the present disclosure include an automated version.

Cartridge: In some embodiments, an elastomeric bladder component is disposed within a durable housing forming the cartridge (110). In some embodiments, the elastomeric material is urethane. In some embodiments, the elastomeric material is polyurethane. In some embodiments, the elastomeric material is silicone. In some embodiments, the elastomeric material must be of suitable hardness and perform effectively in a temperature range from 4 degrees C. to 50 degrees C.

Septum: In some embodiments, the septum (130) is constructed from elastomeric material. In some embodiments, the septum (130), once pierced by the needle (145) of the syringe (140) is tight around the body of the needle (145) making removal difficult. In some embodiments, the septum (130) squeezes on the needle (145) of the syringe (140) to prevent regurgitation of the fluid thus mitigating risk of biohazard contamination.

Ratchet Mechanism: In some embodiments, the ratchet mechanism (190) is adapted to provide rotation by turning the dial (170) forward until it clicks with tactile feedback. In some embodiments, it can turn forward no more upon reaching this click. In some embodiments, the user must turn the dial (170) backwards to release the dial (170) for rotation into the second forward position. In some embodiments, once the dial (170) is turned backwards until it clicks with tactile feedback, the user cannot turn the dial (170) backwards any more upon reaching the click. In some embodiments, the user may now progress to the next stage by turning forwards. In some embodiments, the ratchet mechanism (190) prevents the user from turning the dial (170) backwards once it has completed all four stages.

Fluid Mechanics of the Sample to be investigated: In some embodiments, a large bubble or multiple bubbles are generated to push the sample to be investigated close to the surface of the region of interrogation (180) as the sample to be investigated passes through. In some embodiments, the flow regime is modified slug flow. In some embodiments, the flow regime is modified Taylor flow. In some embodiments, the flow regime is dispersed-bubble or bubble flow. In some embodiments, it is desirable to have a bubble longer than the channel is wide as a means to deposit the specific molecules on the surface of the windows. In some embodiments, the flow regime is elongated bubble or churn flow. In some embodiments, the flow regime is stratified smooth flow. In some embodiments, the flow regime is stratified wavy flow. In some embodiments, the flow regime is annular flow. In some embodiments, as the cartridge is shaken or agitated, the gas (bubble) rises creating a thin film on the surface of the top window (181) and the bottom window (182) of the dual window region of interrogation (180). In some embodiments, the microbial pathogens are forced close to the surface to improve capture efficiency. In some embodiments, the larger orifice on the side wall of the dial (170) is adapted to prevent bubble trapping in flow from the reagent chamber (160) to the dial (170).

In some embodiments, a plant metabolite is adhered to the top window (181) and the bottom window (182) of the dual window region of interrogation (180) to chemically strip out medically important microbial pathogens by causing them to stick to the window. In some embodiments, a wide range of chemicals can be adhered to the top window (181) and the bottom window (182) of the dual window region of interrogation (180) for capturing other compounds including DNA, glucose, hormones, and the like.

In some embodiments, the dial (170) comprises two ridges disposed on the dial side wall thereon that set into two grooves on in the cartridge forming a seal. In some embodiments, o-rings can be used as an alternate sealing method for the dial (170). In some embodiments, the top window (181) and the bottom window (182) of the dual window region of interrogation (180) are constructed of quartz. In some embodiments, the top window (181) and the bottom window (182) of the dual window region of interrogation (180) are planar. In some embodiments, the top window (181) and the bottom window (182) of the dual window region of interrogation (180) are cylindrical or tubular.

In some embodiments, alternate uses for the system (100) include, but are not limited to DNA analysis, analysis of modified proteins indicative of medical emergencies (e.g. impending heart attack), analysis of circulating cancer cells, analysis of hormones, analysis of cytokines, analysis of antibodies indicative of exposure to disease-causing microorganisms.

In some embodiments, a medically important analyte includes, but is not limited to, a component of blood or another body fluid. In some embodiments, analytes of medical interest include, but are not limited to, proteinaceous toxins, circulating cancer cells, nucleic acids, hormones, cytokines, or modified proteins. In some embodiments, some non-limiting examples of analytes of medical interest include as follows: proteinaceous toxins, circulating cancer cells, nucleic acids, hormones, cytokines, or modified proteins. In some embodiments, examples of microbial pathogens that can be captured using heparan sulfate or lignosulfonic acid are: HIV-1, hepatitis B virus, *Staphylococcus aureus, Plasmodium* spp., *Leishmania* spp., vaccinia virus, and *Neisseria gonorrhoeae*.

In some embodiments, the cartridge utilizes open channel flow. In some embodiments, the cartridge utilizes lateral flow. In some embodiments, if the capture ligand is heparan sulfate or lignosulfonic acid, the injected sample must is not presented in a syringe that contains a heparin coating. In some embodiments, the syringe contains another type of coating to inhibit clotting, such as citric acid or EDTA.

In some embodiments, the targeted analyte is analyzed through the region of interrogation (180) via x-ray equipment. In some embodiments, the targeted analyte is analyzed through the region of interrogation (180) via magnetic techniques. In some embodiments, the targeted analyte is analysed through the region of interrogation (180) via radio waves. In some embodiments, the targeted analyte is analyzed through the region of interrogation (180) via visual inspection.

In some embodiments, there are four positions, the first position, the second position or the primary next position, the third position or the secondary next position, and the final position. In some embodiments, there can be a number of positions. In some embodiments, in the primary next position the device is shaken or rocked to flush the fluid containing dyes or ligand-dye conjugates across the region of interrogation (180) between the next anterior reagent chamber (161) and the next posterior reagent chamber. In some embodiments, before rotation to the next position, the fluid is drained into the posterior reagent chamber. In some embodiments, in the secondary next position. In some embodiments, upon shaking or rocking, bubbles due to Taylor, or Slug flow through the dial channel (175) are formed and passed through the dial channel (175) causing a wash solution to be transported in close proximity to inside surfaces of the region of interrogation (180) containing the dye-labeled pathogens or other analytes captured on the surface. In some embodiments, before rotation to the final position, the fluid is drained into the posterior reagent chamber.

In some embodiments, the fluid mechanics are manually driven in the cartridge (110). In some embodiments, the fluid mechanics are driven using strategically positioned elastomeric reservoirs that upon compression from an outside source, drive the fluid into a desired reagent chamber (160). In some embodiments, the fluid mechanics are driven using strategically positioned elastomeric buttons attached to a specific reagent chamber (160) that upon compression from an outside source, drive the fluid into a desired reagent chamber (160).

In some embodiments, radial and axial compression seals are integrated into the cartridge to prevent fluid migration within or to the outside of the cartridge. In some embodiments, radial and axial compression seals are integrated into the syringe port, reagent chamber, the dial, and the region of interrogation.

In some embodiments, the system comprises particulate (or particles) located within the reagent chamber to aid capture efficiency. The use of particles may be for improved detection and capture of low concentration targets. In some embodiments, the use of nano, micro, or other sized particles has multiple distinct effects that help minimize the path of diffusion and tailor fluid viscosity.

In some embodiments, the present disclosure comprises a disposable device with an effective ligand coated window and dye inside that allows for the injecting of an analyte fluid into the device via a captively fastened and sealed syringe, introducing bubbles which thereby effectively coat the window with dye coated targeted pathogens for analysis by another means.

As used herein, the term "about" refers to plus or minus 10% of the referenced number.

The disclosures of the following U.S. Patents are incorporated in their entirety by reference herein: U.S. Pat. No. 6,750,006; U.S. Pat. No. 6,780,602; U.S. Pat. No. 7,186,990; U.S. Pat. No. 7,211,377; U.S. Pat. No. 7,824,883; and U.S. Patent Pub. No. 2012/0111719.

Various modifications of the disclosure, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the disclosure described herein using the phrase "comprising" includes embodiments that could be described as "consisting of", and as such the written description requirement for claiming one or more embodiments of the present disclosure using the phrase "consisting of" is met.

We claim:

1. A system comprising:
   (a) a cartridge having two or more reagent chambers disposed therein, wherein each reagent chamber comprises a through-port;
   (b) a cylindrical dial having a dial channel with a transparent region of interrogation centrally disposed therein, wherein the dial facilitates a sequential introduction of various fluids contained in the reagent chambers into a sample to be investigated through the dial channel; and
   (c) a syringe port disposed on an outside of the cartridge and fluidly connected to a syringe channel disposed within the cartridge, wherein an interior end of the syringe channel comprises an injection port that is fluidly coupled to the region of interrogation;
   wherein the reagent chambers are positioned around the cylindrical dial such that when the cylindrical dial is rotated, the dial channel sequentially aligns with each reagent chamber through-port, wherein when the reagent chamber through-port aligns with the dial channel, a reagent from the reagent chamber can flow into the region of interrogation; and
   wherein the dial channel is disposed through the dial from a first location on a dial side wall to a second location on an opposing side of the dial side wall, wherein the dual window region of interrogation is centrally disposed in the dial, wherein the dial channel is disposed between a top window and a bottom window of the dual window region of interrogation.

2. The system of claim 1, wherein the dial is centrally disposed in the cartridge, wherein the dial extends through the cartridge to engage an inside wall of a cartridge bottom surface, wherein the dial comprises a dial thickness from a dial top surface to the dial bottom surface about equal to a cartridge thickness from a cartridge top surface to the cartridge bottom surface.

3. The system of claim 1, wherein a cross-section of the dial channel is greater at the first location on the dial side wall and the second location on the dial side wall than a cross-section of the dial channel between the top window and the bottom window of the region of interrogation, wherein a cross-sectional area of the dial channel reduces towards the region of interrogation and increases towards the dial side wall to create bubbles upon agitation of the sample to be investigated.

4. The system of claim 1, wherein the sample to be investigated comprises microbial pathogens or other analytes of interest, and wherein a ligand is deposited in the region of interrogation on an inside surface of a top window and an inside surface of a bottom window for collecting microbial pathogens or other analytes of interest from the sample to be investigated, wherein the ligand interacts with the microbial pathogens or other analytes of interest causing them to collect on the inside surface of the top window and the inside surface of the bottom window from the sample to be investigated.

5. The system of claim 1, wherein the system further comprises a light microscope cartridge, wherein a light microscope is used with the cartridge for detection.

6. The system of claim 1, wherein the sample to be investigated comprises microbial pathogens or other analytes of interest, and wherein distilled or lightly buffered distilled water is disposed in a reagent chamber for combining with the targeted analyte.

7. The system of claim 1, wherein the sample to be investigated comprises microbial pathogens or other analytes of interest, and wherein a dye conjugate is disposed in a reagent chamber for combining with the targeted analyte.

8. The system of claim 1, wherein the sample to be investigated comprises microbial pathogens or other analytes of interest, and wherein a lignosulfonic acid-fluorescent dye conjugate or heparin sulfate-fluorescent dye conjugate is disposed in a reagent chamber for combining with the targeted analyte resulting with the targeted analyte being labelled with that fluorescent dye.

9. The system of claim 1, wherein the sample to be investigated comprises microbial pathogens or other analytes of interest, and wherein a wash buffer or distilled water is disposed in a reagent chamber for combining with the targeted analyte.

10. The system of claim 1, wherein a locking tab is slidably disposed in a locking tab channel, wherein the locking tab channel comprises a locking tab channel anterior side and a locking tab channel posterior side, and the locking tab channel is disposed on a cartridge posterior end, wherein a first locking tab stop is disposed on the locking tab channel posterior side adjacent to the syringe port to hold the locking tab into a first, open position, wherein a second locking tab stop is disposed on the locking tab channel posterior side at a distance equal to a locking tab length from an opposite syringe channel side wall to hold the locking tab into a second, closed position, and wherein a tensioning projection is disposed on the locking tab channel anterior side between the first locking tab stop and the second locking tab stop to provide tension on the locking tab in the first position or the second position.

11. The system of claim 1, wherein the dial comprises a first dial indentation and a second dial indentation disposed on a dial top surface thereon adapted to receive a finger or a thumb of a user inserted therein for manually rotating the dial.

12. The system of claim 1, wherein the dial comprises a ratchet mechanism having a grooved track disposed on a cartridge inside surface and a mated spring-biased pin for following the grooved track disposed on the dial.

13. A system comprising:
   (a) a cartridge having two or more reagent chambers disposed therein, wherein each reagent chamber comprises a through-port;
   (b) a cylindrical dial having a dial channel with a transparent region of interrogation centrally disposed therein, wherein the dial facilitates a sequential introduction of various fluids contained in the reagent chambers into a sample to be investigated through the dial channel; and
   (c) a syringe port disposed on an outside of the cartridge and fluidly connected to a syringe channel disposed within the cartridge, wherein an interior end of the syringe channel comprises an injection port that is fluidly coupled to the region of interrogation;

wherein the reagent chambers are positioned around the cylindrical dial such that when the cylindrical dial is rotated, the dial channel sequentially aligns with each reagent chamber through-port, wherein when the reagent chamber through-port aligns with the dial channel, a reagent from the reagent chamber can flow into the region of interrogation; and wherein a locking tab is slidably disposed in a locking tab channel, wherein the locking tab channel comprising a locking tab channel anterior side and a locking tab channel posterior side is disposed on a cartridge posterior end, wherein a first locking tab stop is disposed on the locking tab channel posterior side adjacent to the syringe port to hold the locking tab into a first, open position, wherein a second locking tab stop is disposed on the locking tab channel posterior side at a distance equal to a locking tab length from an opposite syringe channel side wall to hold the locking tab into a second, closed position, wherein a tensioning projection is disposed on the locking tab channel anterior side between the first locking tab stop and the second locking tab stop to provide tension on the locking tab in the first position or the second position.

14. The system of claim 13, wherein a septum is disposed on the interior end of the syringe channel.

15. The system of claim 13, wherein a first collar is disposed in the syringe channel adjacent to the syringe port and a second collar is disposed in the syringe channel proximal to the first collar.

16. The system of claim 13, wherein a syringe channel volume is greater than a volume of a syringe for safely containing an unintentional discharge from the syringe before piercing the septum.

17. The system of claim 13, wherein the sample to be investigated comprises microbial pathogens or other analytes of interest, and wherein a ligand is deposited in the region of interrogation on an inside surface of a top window and an inside surface of a bottom window for collecting microbial pathogens or other analytes of interest from the sample to be investigated, wherein the ligand interacts with the microbial pathogens or other analytes of interest causing them to collect on the inside surface of the top window and the inside surface of the bottom window from the sample to be investigated.

18. The system of claim 13, wherein the dial comprises a ratchet mechanism having a grooved track disposed on a cartridge inside surface and a mated spring-biased pin for following the grooved track disposed on the dial.

19. A system comprising:
(a) a cartridge having two or more reagent chambers disposed therein, wherein each reagent chamber comprises a through-port;
(b) a cylindrical dial having a dial channel with a transparent region of interrogation centrally disposed therein, wherein the dial facilitates a sequential introduction of various fluids contained in the reagent chambers into a sample to be investigated through the dial channel; and
(c) a syringe port disposed on an outside of the cartridge and fluidly connected to a syringe channel disposed within the cartridge, wherein an interior end of the syringe channel comprises an injection port that is fluidly coupled to the region of interrogation;

wherein the reagent chambers are positioned around the cylindrical dial such that when the cylindrical dial is rotated, the dial channel sequentially aligns with each reagent chamber through-port, wherein when the reagent chamber through-port aligns with the dial channel, a reagent from the reagent chamber can flow into the region of interrogation; and wherein the dial comprises a ratchet mechanism having a grooved track disposed on a cartridge inside surface and a mated spring-biased pin for following the grooved track disposed on the dial.

20. The system of claim 19, wherein the sample to be investigated comprises microbial pathogens or other analytes of interest, and wherein a ligand is deposited in the region of interrogation on an inside surface of a top window and an inside surface of a bottom window for collecting microbial pathogens or other analytes of interest from the sample to be investigated wherein the ligand interacts with the microbial pathogens or other analytes of interest causing them to collect on the inside surface of the top window and the inside surface of the bottom window from the sample to be investigated.

* * * * *